United States Patent
Miyasa et al.

(10) Patent No.: US 10,441,163 B2
(45) Date of Patent: Oct. 15, 2019

(54) OPHTHALMIC DIAGNOSIS SUPPORT APPARATUS AND OPHTHALMIC DIAGNOSIS SUPPORT METHOD

(71) Applicant: CANON KABUSHIKI KAISHA, Tokyo (JP)

(72) Inventors: Kazuhiro Miyasa, Yokohama (JP); Hiroshi Imamura, Kyoto (JP)

(73) Assignee: Canon Kabushiki Kaisha, Tokyo (JP)

(*) Notice: Subject to any disclaimer, the term of this patent is extended or adjusted under 35 U.S.C. 154(b) by 8 days.

(21) Appl. No.: 15/822,306

(22) Filed: Nov. 27, 2017

(65) Prior Publication Data
US 2018/0070815 A1   Mar. 15, 2018

Related U.S. Application Data

(62) Division of application No. 14/122,265, filed as application No. PCT/JP2012/069524 on Jul. 25, 2012, now Pat. No. 9,848,769.

(30) Foreign Application Priority Data

Aug. 1, 2011 (JP) ................. 2011-168603

(51) Int. Cl.
  *A61B 3/10* (2006.01)
  *A61B 3/14* (2006.01)
  (Continued)

(52) U.S. Cl.
  CPC ............ *A61B 3/102* (2013.01); *A61B 3/0041* (2013.01); *A61B 3/1005* (2013.01); *A61B 3/12* (2013.01);
  (Continued)

(58) Field of Classification Search
  CPC ....... A61B 3/1005; A61B 3/14; A61B 3/0041; A61B 3/102; A61B 3/12; A61B 3/1233;
  (Continued)

(56) References Cited

U.S. PATENT DOCUMENTS 7,566,128 B2  7/2009  Tsukada et al.
7,857,449 B2  12/2010  Imamura et al.
(Continued)

FOREIGN PATENT DOCUMENTS

CN  1939208 A  4/2007
JP  2009-279031 A  12/2009
(Continued)

OTHER PUBLICATIONS

Nov. 16, 2012 International Search Report and Written Opinion in International Patent Appln. No. PCT/JP2012/069524.
(Continued)

*Primary Examiner* — Jordan M Schwartz
(74) *Attorney, Agent, or Firm* — Venable LLP

(57) ABSTRACT

Provided is an ophthalmic diagnosis support apparatus which enables an operator to easily acquire a tomographic image suitable for detailed observation of a candidate lesion without spending time and effort to search for the candidate lesion. The ophthalmic diagnosis support apparatus includes an acquiring unit for acquiring a wide-range image of a fundus, a candidate lesion detection unit for detecting the candidate lesion on the fundus by analyzing the wide-range image, a calculating unit for determining a degree of abnormality of the candidate lesion based on a result of the detection of the candidate lesion, and an acquiring position setting unit for setting an acquiring position of the tomographic image of the fundus based on the degree of abnormality of the candidate lesion.

12 Claims, 22 Drawing Sheets

(51) Int. Cl.
  *G06K 9/32* (2006.01)
  *A61B 3/12* (2006.01)
  *A61B 3/00* (2006.01)
  *G06T 7/00* (2017.01)
  *G06K 9/00* (2006.01)

(52) U.S. Cl.
  CPC ............ *A61B 3/14* (2013.01); *G06K 9/00604* (2013.01); *G06K 9/3241* (2013.01); *G06T 7/0012* (2013.01); *G06T 2207/10101* (2013.01); *G06T 2207/30041* (2013.01)

(58) Field of Classification Search
  CPC ............. A61B 3/1241; G06K 9/00604; G06K 9/3233; G06K 9/3241; G06T 7/0012; G06T 2207/10101; G06T 2207/30041
  See application file for complete search history.

(56) References Cited

U.S. PATENT DOCUMENTS

| | | | |
|---|---|---|---|
| 7,980,695 B2 | 7/2011 | Imamura et al. | |
| 8,322,854 B2 | 12/2012 | Imamura et al. | |
| 8,596,785 B2 | 12/2013 | Imamura et al. | |
| 9,307,903 B2 | 4/2016 | Imamura | |
| 9,351,650 B2 | 5/2016 | Uji et al. | |
| 9,820,650 B2 | 11/2017 | Uji et al. | |
| 2004/0258285 A1* | 12/2004 | Hansen | G06T 7/0012 382/128 |
| 2006/0187462 A1 | 8/2006 | Srinivasan et al. | |
| 2007/0070295 A1 | 3/2007 | Tsukada et al. | |
| 2008/0068560 A1 | 3/2008 | Knighton et al. | |
| 2010/0202677 A1 | 8/2010 | Imamura et al. | |
| 2010/0208204 A1 | 8/2010 | Imamura et al. | |
| 2011/0007957 A1 | 1/2011 | Sakagawa | |
| 2011/0034803 A1* | 2/2011 | Stetson | G06T 15/08 600/425 |
| 2011/0051088 A1 | 3/2011 | Shimizu et al. | |
| 2011/0080560 A1 | 4/2011 | Imamura et al. | |
| 2011/0137157 A1 | 6/2011 | Imamura et al. | |
| 2011/0170062 A1 | 7/2011 | Isogai et al. | |
| 2011/0181614 A1* | 7/2011 | Chang | G06T 7/0012 345/595 |
| 2011/0200242 A1 | 8/2011 | Takama et al. | |
| 2011/0267584 A1 | 11/2011 | Imamura et al. | |
| 2012/0063660 A1 | 3/2012 | Imamura et al. | |
| 2012/0130270 A1 | 5/2012 | Imamura et al. | |
| 2012/0183188 A1* | 7/2012 | Moriya | G06F 19/321 382/128 |
| 2012/0194782 A1 | 8/2012 | Imamura | |
| 2013/0057827 A1 | 3/2013 | Imamura et al. | |
| 2013/0257910 A1* | 10/2013 | Park | G06K 9/00 345/672 |
| 2014/0240667 A1 | 8/2014 | Uji et al. | |
| 2014/0240668 A1 | 8/2014 | Uji et al. | |
| 2014/0240669 A1 | 8/2014 | Imamura | |

FOREIGN PATENT DOCUMENTS

| | | |
|---|---|---|
| JP | 2010-035607 A | 2/2010 |
| WO | 2009/011088 A1 | 1/2009 |

OTHER PUBLICATIONS

Feb. 4, 2014 International Preliminary Report on Patentability in International Patent Appln. No. PCT/JP2012/069524.

Jun. 4, 2015 Chinese Official Action in Chinese Patent Appln. No. 201280038089.X.

* cited by examiner

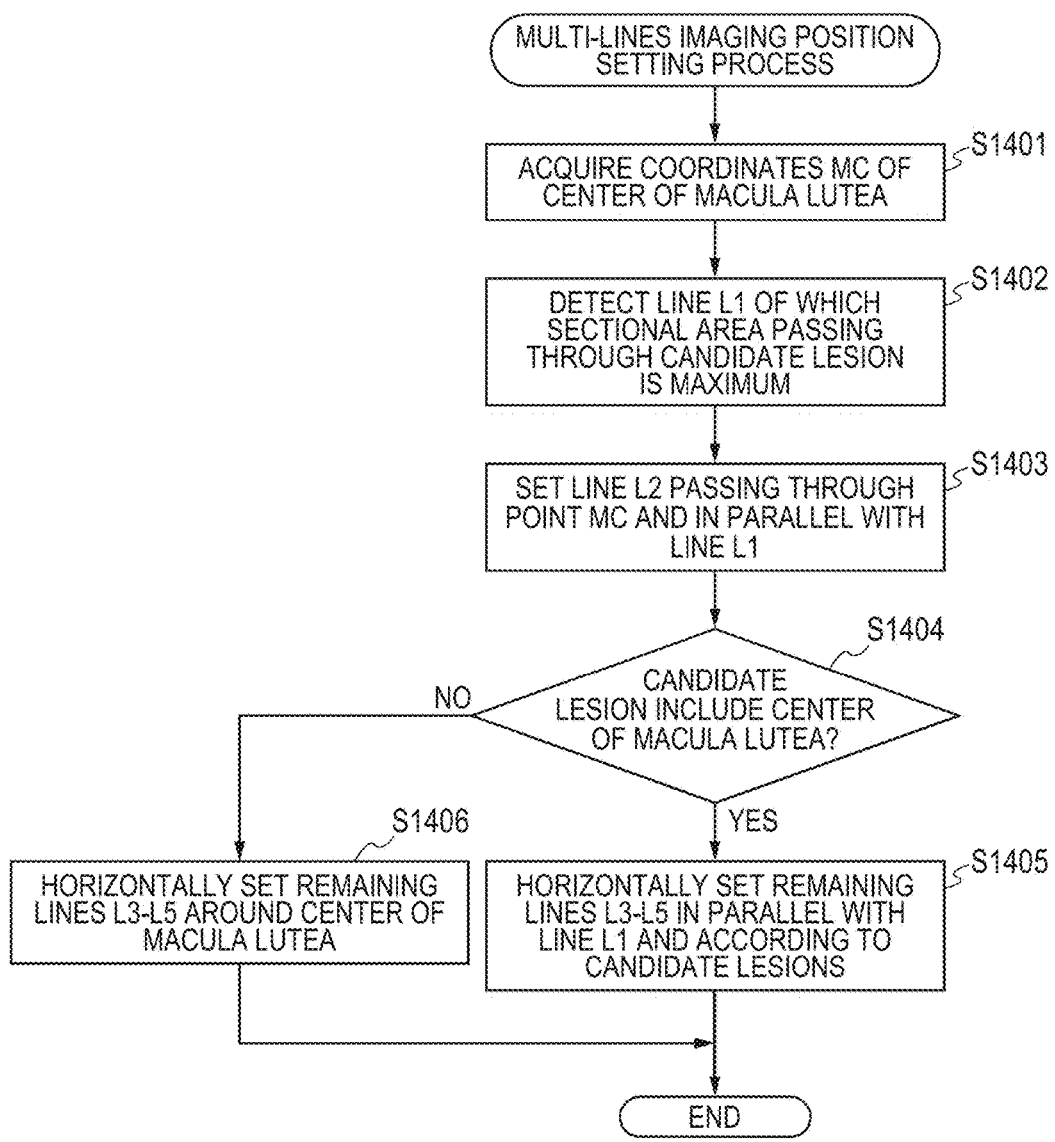

OPHTHALMIC DIAGNOSIS SUPPORT APPARATUS AND OPHTHALMIC DIAGNOSIS SUPPORT METHOD

This application is a division of application Ser. No. 14/122,265 filed Nov. 26, 2013, which was the National Stage of International Application No. PCT/JP2012/069524 filed Jul. 25, 2012.

TECHNICAL FIELD

The present invention relates to an image processing apparatus for supporting eye imaging, and more particularly, to an ophthalmic diagnosis support apparatus and an ophthalmic diagnosis support method for supporting ophthalmic diagnosis by performing image processing using a tomographic image of an eye, and further to a program for performing the ophthalmic diagnosis support method and a storage medium having the program stored thereon.

BACKGROUND ART

For early diagnosis of lifestyle-related diseases or diseases ranking as leading causes of loss of eyesight, eye examination is widely performed. An eye tomographic imaging apparatus such as an optical coherence tomography (OCT) enables three-dimensional observation of an internal state of a retinal layer, and is therefore expected to be useful for more accurate diagnosis of the diseases.

FIG. 1 illustrates a schematic diagram of a tomographic image of a macula lutea portion of a retina taken by the OCT. In FIG. 1, "F" represents a fundus image, "$R_{XY}$" represents an imaging range on the fundus, "MC" represents a center of the macula lutea, "$T_1$" to "$T_n$" represent two-dimensional tomographic images constituting a volume image (B-scan image, hereinafter referred to as tomographic image), and "A" represents a scan line (A-scan line) in a depth direction of the retina ("z" direction). Further, the tomographic image $T_n$ shows an internal limiting membrane 1, a nerve fiber layer 2, a ganglion cell layer 3, an inner plexiform layer 4, an inner nuclear layer 5, an outer plexiform layer 6, an outer nuclear layer 7, an external limiting membrane 8, a photoreceptor inner/outer segment junction 9, and a retinal pigment epithelium boundary 10. When this tomographic image is input, for example, in a case where a thickness between the internal limiting membrane 1 and the retinal pigment epithelium boundary 10, that is, a thickness of the retina, can be measured, this can be useful for diagnosis of various diseases in which a visual disorder is caused by a variation of the thickness of the retina. This imaging method of acquiring a volume image by taking images of a two-dimensional range on the fundus is referred to as three-dimensional (3D) scan.

In addition, the OCT imaging uses an imaging method of repeatedly imaging an irradiated area on the same line of the fundus, and calculating an arithmetic mean of the obtained tomographic images so as to output a high-definition tomographic image with little noise. Hereinafter, this method is referred to as line scan. With this imaging method, it is possible to closely observe an anatomical structure inside the retinal layer at the center of the macula lutea or in a lesion region, which is an important region for diagnosis of fundus diseases. In the imaging of the line scan, in addition to a single tomographic image, multiple tomographic images may be taken by setting multiple lines as an imaging area on the fundus.

In this way, on a clinical site, two types of imaging methods are used in combination in many cases, that is, the 3D scan for acquiring a wide-range volume image so as to prevent unintended omission of a tomographic image, and the line scan for acquiring a high-definition image for detailed observation of the lesion.

In this case, in the line scan, only the tomographic image corresponding to a specific line area on the fundus is acquired. Therefore, it is necessary to appropriately set an imaging position so that the anatomical structures of the center of the macula lutea and the lesion region are included in the tomographic image. However, in the conventional OCT apparatus, it has been necessary for an operator to manually set the imaging position, and hence much time and effort has been required to search for the center of the macula lutea and the lesion position on the fundus. In addition, there has been a risk that an appropriate position cannot be imaged because the operator overlooks the lesion or erroneously sets a position shifted from the center of the macula lutea as the imaging position.

To address this problem, Patent Literature 1 discloses a technology in which a position of a characteristic region is identified in a tomographic image acquired through preliminary measurement, and then an irradiation position of a signal light is changed based on the position of the characteristic region so that the characteristic region is rendered at a predetermined position in a frame through main measurement. Specifically, a position of the center of the macula lutea or a dent indicating a center of an optic nerve mamilla is detected as the characteristic region in the tomographic image through the preliminary measurement, and hence the irradiation position is determined so that the position is rendered at the predetermined position in the frame through the main measurement.

In addition, Patent Literature 2 discloses a technology of detecting a candidate lesion in a wide-range image of the fundus, and determining a spatial range of a tomographic image to be taken, a scan line interval, and a scan order and direction based on a type and a range of the detected candidate lesion. Further, there is also disclosed a technology of determining whether or not it is necessary to acquire the tomographic image according to seriousness of the candidate lesion or a region in which the candidate lesion occurs.

However, the conventional technologies have the following problems. In the technology disclosed in Patent Literature 1 described above, in a case where the characteristic region has a structure extending in an isotropic manner from the center (dent), such as the macula lutea portion or the optic nerve mamilla portion, when only the center position is identified, the irradiation position can be determined so that the character is rendered in the tomographic image. However, in a case where the characteristic region is a lesion, the lesion does not necessarily have an isotropic extension from its center position. For instance, in a case of a macula lutea edema observed in a diabetic retinopathy, blood flows out of a capillary aneurysm or a blood vessel so that a low brightness area called a cyst occurs in the retina, and hence the retina swells. In this case, the retina swells not in an isotropic manner from the center position of the lesion, but in various different manners according to a position or a degree of the generated cyst. Therefore, when the imaging position is automatically set in the method described in Patent Literature 1, the acquired tomographic image may include a part of the lesion but does not necessarily have the above-mentioned feature of the macula lutea edema rendered therein. Therefore, this is not necessarily an appropriate tomographic image for detailed observation of the lesion.

In addition, in the technology disclosed in Patent Literature 2, in a case where the 3D scan image is taken at close scan intervals, when the spatial range of the tomographic image is determined according to extension of the lesion, a tomographic image useful for diagnosis of a lesion can be included in the acquired volume image. However, in a case where multiple line scan images which assume the use of the arithmetic mean of the tomographic images as described above are taken, the tomographic images are taken at separate scan intervals, and therefore do not necessarily include the tomographic image capturing the above-mentioned feature of the lesion.

CITATION LIST

Patent Literature

PTL 1: Japanese Patent Application Laid-Open No. 2009-279031
PTL 2: Japanese Patent Application Laid-Open No. 2010-35607

SUMMARY OF INVENTION

Technical Problem

The present invention has been made in view of the above-mentioned problems, and an object thereof is to provide an ophthalmic diagnosis support apparatus and an ophthalmic diagnosis support method, which enable an operator to easily acquire a tomographic image suitable for detailed observation of a candidate lesion without spending time and effort to search for the candidate lesion.

In order to achieve the above-mentioned object, according to an exemplary embodiment of the present invention, there is provided an ophthalmic diagnosis support apparatus including: an acquiring unit for acquiring a fundus image; a candidate lesion detection unit for detecting a candidate lesion on a fundus by analyzing the fundus image; a calculating unit for determining a degree of abnormality of the candidate lesion based on a result of the detection of the candidate lesion; and an acquiring position setting unit for setting an acquiring position of a tomographic image of the fundus based on the degree of abnormality of the candidate lesion.

Advantageous Effects of Invention

According to the present invention, the acquiring position of the tomographic image is automatically set according to the degree of abnormality of the candidate lesion on the fundus. Therefore, the operator can easily acquire the tomographic image suitable for detailed observation of the candidate lesion without spending time and effort to manually search for the candidate lesion.

Further features of the present invention will become apparent from the following description of exemplary embodiments with reference to the attached drawings.

BRIEF DESCRIPTION OF DRAWINGS

FIG. 14 is a flowchart illustrating a process procedure of a second setting method for the multi-line imaging position.

DESCRIPTION OF EMBODIMENTS

First Embodiment

In this embodiment, 3D scan of a macula lutea portion is performed by using an OCT, and a candidate lesion is detected in a taken volume image. Then, a result of the candidate lesion detection is used so as to automatically determine an imaging position for subsequently performing line scan of the macula lutea portion with one line (one line segment, hereinafter, referred to as single line), that is, an acquiring position of a tomographic image so that a feature thereof is best grasped. Thus, the tomographic image suitable for detailed observation of a candidate lesion can be taken without time and effort of an operator. Further, on a clinical site, when both the 3D scan and the line scan are used together, it is possible to use information of the volume image acquired by the 3D scan effectively for determining the imaging position of the line scan.

Figure 2:
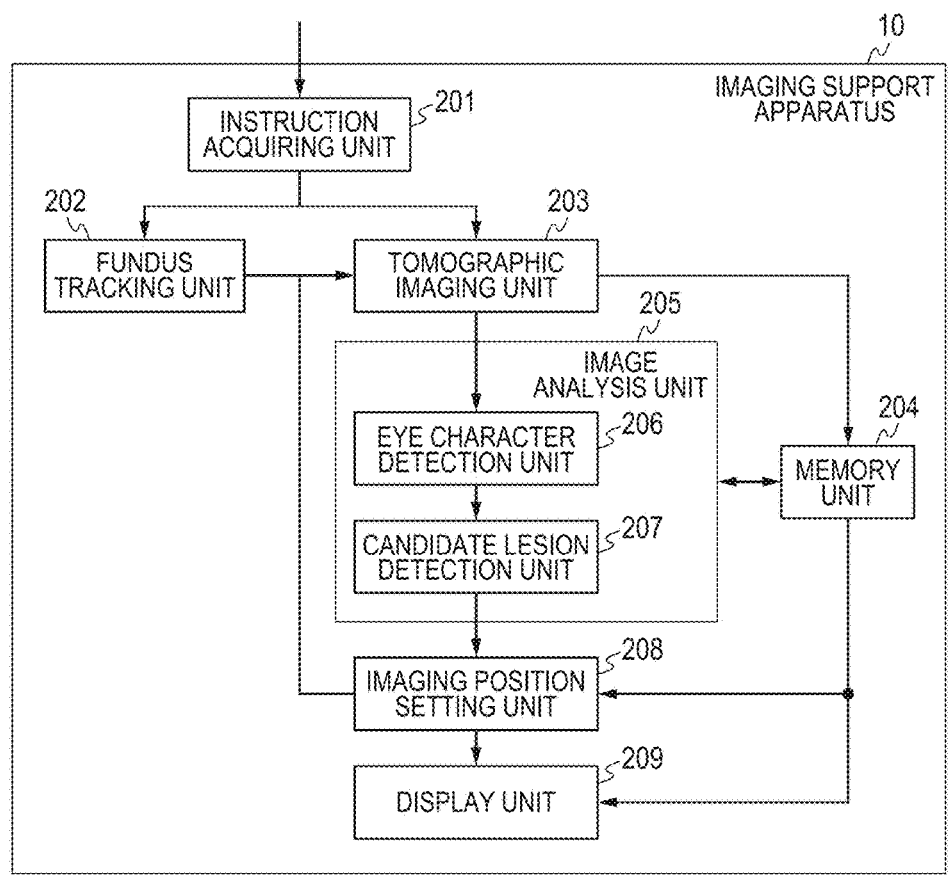
FIG. 2 is a diagram illustrating a functional configuration of an imaging support apparatus according to a first embodiment of the present invention.

FIG. 2 illustrates a functional configuration of an imaging support apparatus (ophthalmic diagnosis support apparatus) 10 according to this embodiment. In FIG. 2, the imaging support apparatus 10 includes an instruction acquiring unit 201, a fundus tracking unit 202, a tomographic imaging unit 203, a memory unit 204, an image analysis unit 205, an imaging position setting unit 208, and a display unit 209. In addition, the image analysis unit 205 includes an eye character detection unit 206 and a candidate lesion detection unit 207. The tomographic imaging unit 203 includes a module functioning as a tomographic image acquiring unit according to the present invention, and the candidate lesion detection unit 207 includes modules functioning respectively as a candidate lesion detection unit and as a calculating unit for calculating a score for evaluating the determined candidate lesion.

Figure 3:
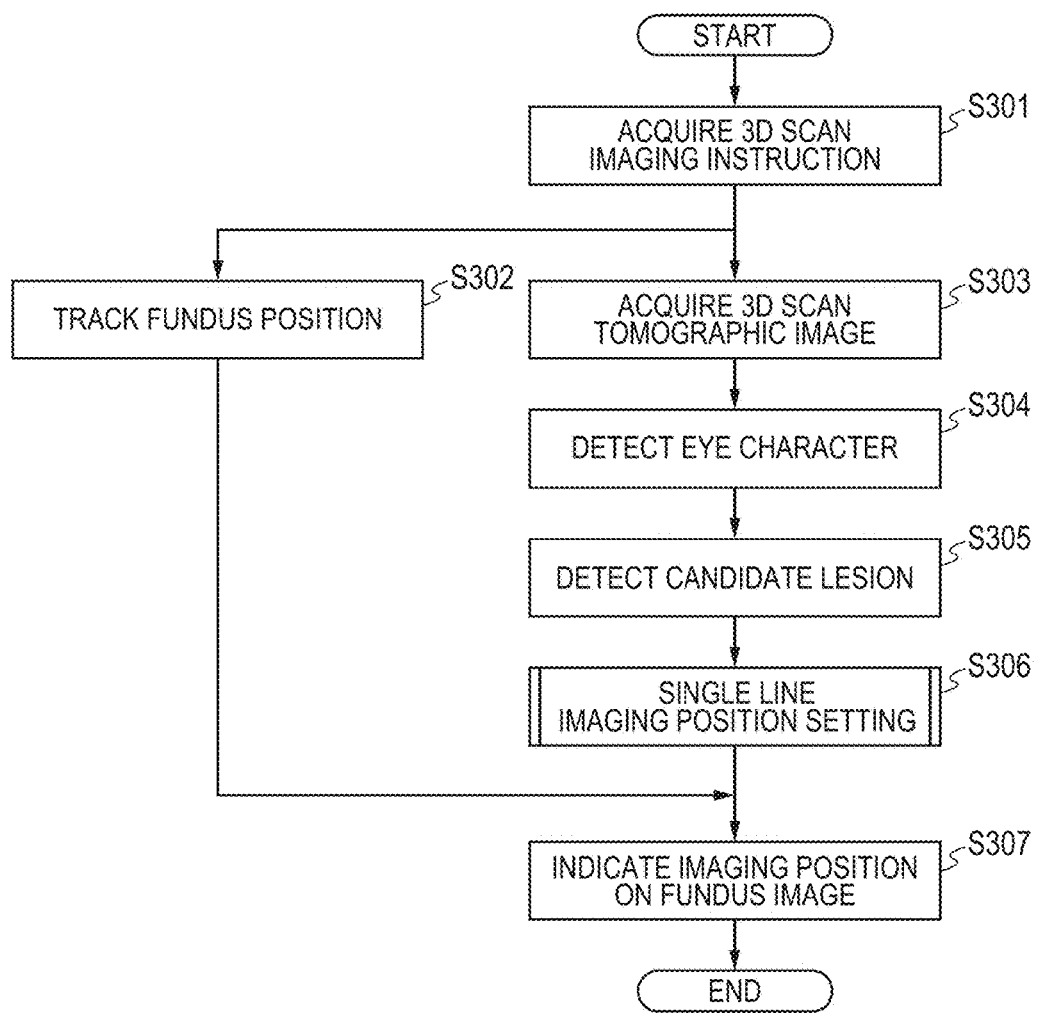
FIG. 3 is a flowchart illustrating a process procedure performed by the imaging support apparatus according to the first embodiment.

FIG. 3 is a flowchart of this embodiment, and a specific process procedure performed by the imaging support apparatus 10 is described with reference to this flowchart.
<Step S301>

In Step S301, the instruction acquiring unit 201 acquires information of a 3D scan imaging instruction of a fundus of an eye to be inspected (not shown) from an operator (not shown), and sends the information to the fundus tracking unit 202 and the tomographic imaging unit 203.
<Step S302>

In Step S302, the fundus tracking unit 202 starts to track the fundus based on the acquired imaging instruction information. Specifically, when the imaging instruction information is acquired, a fundus image of the eye to be inspected is taken as a fundus image A. Further, the fundus image of the eye to be inspected is taken in real time as a fundus image B. The fundus image B is always updated to a latest image as time passes. These fundus images A and B are aligned in real time so as to realize a state where position information of the fundus acquired in real time is always associated with position information of the fundus acquired at the time point of the imaging instruction.

In addition, the process of aligning the fundus images A and B is performed by using the following method specifically. First, a filter emphasizing a linear structure is used so that a blood vessel is extracted from the both images. Here, a line segment emphasizing filter based on a contrast is used, such as a filter for calculating, when a line segment is a structural element, a difference between an average value of brightness values in a structural element and an average value in a local area surrounding the structural element. Here, a multi-valued area obtained as a result of a filtering process may be regarded as a result of blood vessel extraction as it is, or an area after binarization with a certain threshold value may be regarded as a result of blood vessel extraction. The obtained images are referred to as fundus images A' and B', respectively.

In this embodiment, parameters of scales (Sx, Sy), position coordinates (x, y), and rotation (rot) of the fundus image B' are determined with respect to a coordinate system of the fundus image A', and hence the fundus images A' and B' are aligned. In addition, in order to calculate an index of whether or not the images are aligned, a mean squared error of the brightness value of the entire image between the fundus image A' and the fundus image B' is used. In other words, an alignment parameter when the mean squared error becomes smallest is determined.

Note that, the alignment index is not limited to this. Instead of the mean squared error of the brightness value, a correlation coefficient, relative information quantity, or the like may be used. In addition, the original fundus images A and B may be input for alignment as they are.

Next, the fundus image B and the determined alignment parameter are sent to the tomographic imaging unit 203 and the display unit 209 in real time.
<Step S303>

Figure 1:
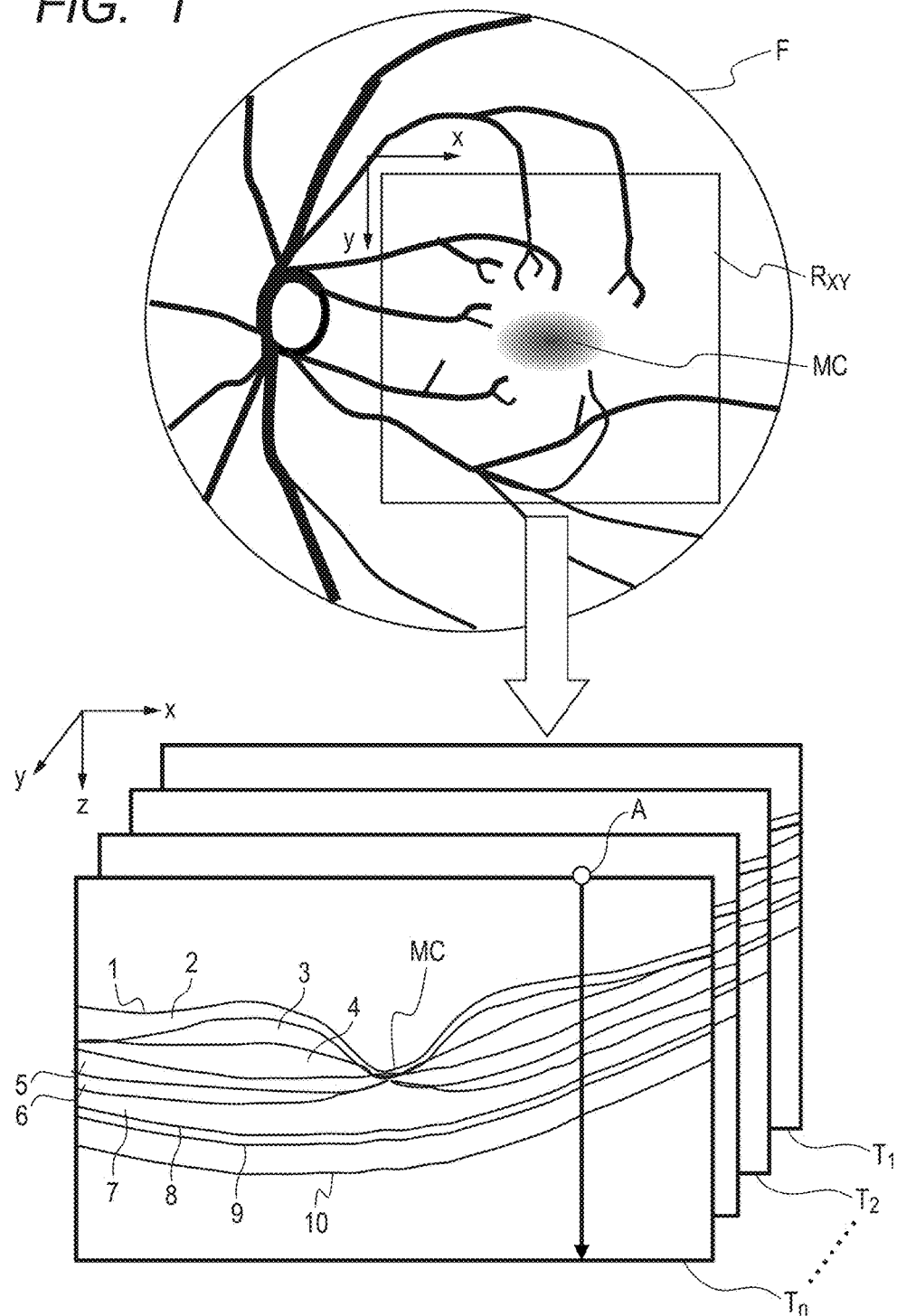
FIG. 1 is a schematic diagram illustrating an imaging range of 3D scan and an eye character in a tomographic image.

In Step S303, the tomographic imaging unit 203 performs the 3D scan of the fundus based on the acquired imaging instruction information, and acquires a wide-range image (image) of the entire fundus range exemplified in, for example, FIG. 1, or a similar wide range. Next, the volume image as the acquired wide-range image is sent to the memory unit 204 and the eye character detection unit 206. In this case, it is supposed that the fundus image A in Step S302 and the 3D scan image in this step are taken simultaneously using the same light source and that positions thereof are associated with each other.
<Step S304>

In Step S304, the eye character detection unit 206 detects, in the volume image, a retinal layer boundary and a position of the center of the macula lutea as an eye character. Note that, the center of the macula lutea is handled as a characteristic region in this embodiment as described above, but the above-mentioned region related to a lesion such as a blood vessel may be regarded as the characteristic region.

Figure 4:
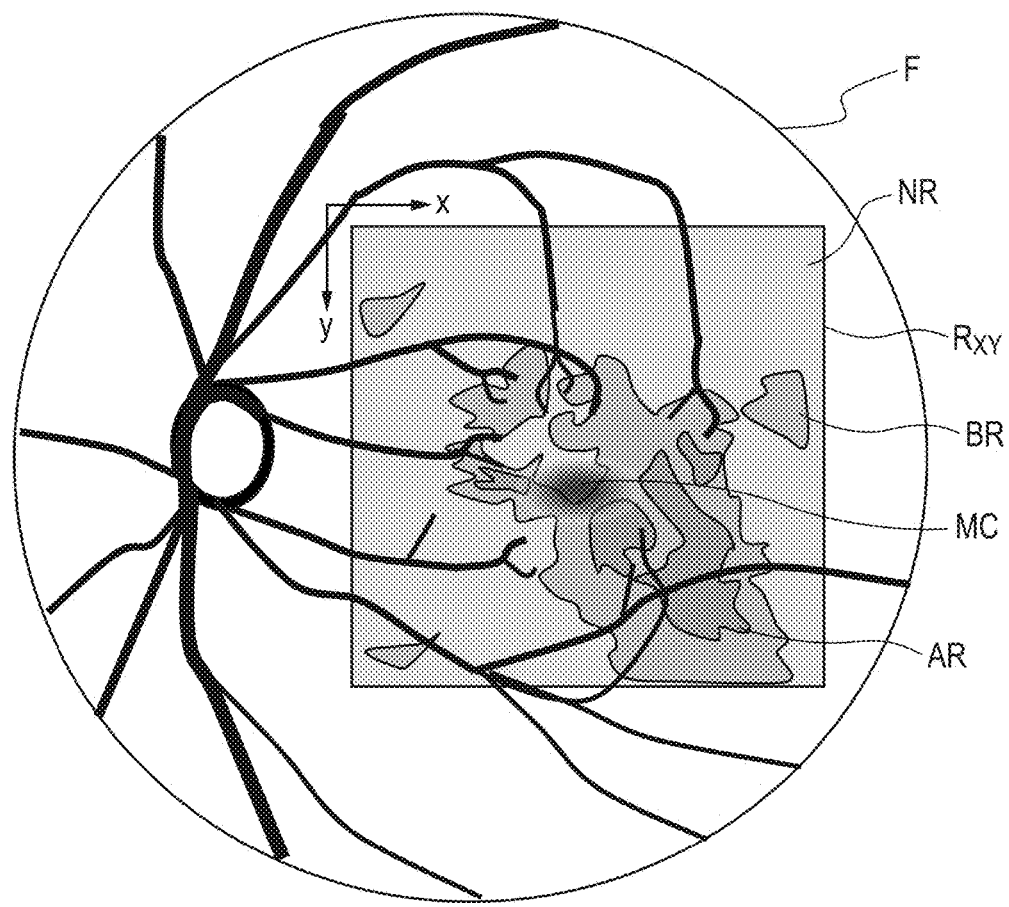
FIG. 4 is a diagram illustrating a significance map of a thickness of a retina superimposed on a fundus image.

In this embodiment, an internal limiting membrane 1 and a retinal pigment epithelium boundary 10 in FIG. 4 are detected as the retinal layer boundary. First, the following process is performed in the unit of each tomographic image constituting the volume image to be processed.

First, a smoothing process is performed on the tomographic image of interest so that noise components are eliminated. Next, an edge enhancement process in a z direction of the tomographic image is performed, and an edge component is detected in the edge-enhanced image. Here, because the internal limiting membrane 1 is a boundary between a corpus vitreum area having a low brightness value and a retinal area having a high brightness value, the internal limiting membrane 1 appears as a particularly strong edge component. In addition, because the retinal pigment epithelium boundary is a boundary on a lower side of a retinal pigment epithelium having particularly high brightness in a retinal layer, the retinal pigment epithelium boundary appears as a strong edge component. Therefore, a brightness profile along an A-scan line is generated from the edge-enhanced image, and two particularly large brightness peaks are detected. Then, positions thereof are identified as the internal limiting membrane 1 and the retinal pigment epithelium boundary 10 in an order from a front side of the retina. This process is performed for all A-scan lines in the image so that lines of the internal limiting membrane 1 and the retinal pigment epithelium boundary 10 are extracted. The data of the layer boundary detected in this way is referred to as layer boundary data.

In addition, the retinal layer boundaries detected in this step are not limited to the internal limiting membrane 1 and the retinal pigment epithelium boundary 10. By adjusting a size of the edge component detected in the image, a target of detection can be any one of the internal limiting membrane 1, a nerve fiber layer 2, a ganglion cell layer 3, an inner plexiform layer 4, an inner nuclear layer 5, an outer plexiform layer 6, an outer nuclear layer 7, an external limiting membrane 8, a photoreceptor inner/outer segment junction 9, and the retinal pigment epithelium boundary 10.

Next, using the following anatomical features of a center of the macula lutea MC, a position of the center of the macula lutea MC is detected.

(i) The center of the macula lutea MC is a dent area on the fundus.
(ii) The retinal blood vessel does not exist at the center of the macula lutea MC.
(iii) The nerve fiber layer 2 does not exist at the center of the macula lutea MC.

In this embodiment, the feature (i) is basically used so that a point at which a z coordinate of the detected internal limiting membrane 1 becomes largest is set as the center of the macula lutea MC. However, in a case of the macula lutea edema, the center of the macula lutea may swell so that the feature (i) is not satisfied. In that case, the features (ii) and (iii) are used so that a position at which the retinal blood vessel does not exist and a thickness of the nerve fiber layer 2 is zero is identified as the center of the macula lutea. The area in which the retinal blood vessel does not exist is determined by using information of the blood vessel area detected in Step S302, and the thickness of the nerve fiber layer 2 is determined by extracting the nerve fiber layer 2 in this step.

Then, the detected layer boundary data is sent to the candidate lesion detection unit 207, and coordinates of a central fossa MC are sent to the memory unit 204.

<Step S305>

In Step S305, the candidate lesion detection unit 207 detects a candidate lesion based on the acquired layer boundary data. For instance, in the case of the macula lutea edema, there is a feature that a thickness of the retina (thickness of the layer between the internal limiting membrane 1 and the retinal pigment epithelium boundary 10) is larger than a thickness in a normal case because of an influence of the lesion such as a cyst generated in the retina. Therefore, in this embodiment, the thickness of the retina is calculated from the boundary data of the internal limiting membrane 1 and the retinal pigment epithelium boundary 10, and the calculated thickness is compared with a normal thickness of the retina so that a part having a particularly large thickness is detected as the candidate lesion.

Specifically, a difference of the z coordinate between the internal limiting membrane 1 and the retinal pigment epithelium boundary 10 is calculated along the A-scan line (in the positive direction of the z axis) in each coordinate of an x-y plane in FIG. 1. In this calculation, this difference value at coordinates (i, j) on the x-y plane is referred to as layer thickness value $t_{i,j}$ of the thickness of the retina.

Next, a layer thickness value determined by the calculation is compared with a normal value database of multiple thicknesses of the retina, which is stored in the memory unit 204 in advance, so as to detect a part having an abnormally large thickness of the retina. Specifically, the coordinates (i, j) on the x-y plane are classified into three areas including a "candidate lesion area", a "boundary area", and a "normal area" according to the following conditions.

(i) "candidate lesion area": in a case where the layer thickness value $t_{i,j}$ is in a range smaller than 1% from the largest value in a data set of the normal value of the thickness of the retina (ii) "boundary area": in a case where the layer thickness value $t_{i,j}$ is in a range smaller than 5% from the largest value other than the range of the condition (i)
(iii) "normal area": in a case where the layer thickness value $t_{i,j}$ is in the remaining range other than the ranges of the conditions (i) and (ii) (5 to 100%)

A map in which the coordinates (i, j) on the x-y plane are classified in this way is referred to as significance map. In this embodiment, a "candidate lesion area" label is assigned to the coordinates (i, j) belonging to the "candidate lesion area" of the above-mentioned significance map, and a data set of the coordinates to which the "candidate lesion area" label is assigned and the layer thickness values $t_{i,j}$ thereof is referred to as candidate lesion information. Therefore, the candidate lesion detection unit 207 also includes a module functioning as an area calculation unit for determining an area of the candidate lesion on the fundus plane based on a result of the candidate lesion detection.

FIG. 4 is a diagram in which the significance map is superimposed on the fundus image in a case where the thickness of the retina has an abnormality. In FIG. 4, "F" represents the fundus image, "$R_{XY}$" represents the imaging area of the 3D scan, "MC" represents the center of the macula lutea, "AR" represents the candidate lesion area, "BR" represents the boundary area, and "NR" represents the normal area.

In addition, the candidate lesion detected in this step is not limited to the above-mentioned candidate lesion area AR. An area including the areas AR and BR may be detected as the candidate lesion. Further, the layer thickness to be calculated for detecting the candidate lesion is not limited to the thickness of the retina. For instance, in a case where the photoreceptor layer has a defect, a layer between the photoreceptor inner/outer segment junction 9 and the retinal pigment epithelium boundary 10 in FIG. 1 becomes thin. Therefore, in this case, an area where the layer thickness between the photoreceptor inner/outer segment junction 9 and the retinal pigment epithelium boundary becomes abnormally thinner than the normal thickness is detected as the candidate lesion. In addition, the candidate lesion is not limited to an abnormal area of the layer thickness value. For instance, a cyst area observed in a case of macula lutea edema is rendered as an area having lower brightness than the surrounding retinal layer area on the tomographic image. Therefore, it is possible to detect the low brightness area by a threshold value process and to set the area as the candidate lesion. Further, in a case of diabetic retinopathy, fat leaking from a blood vessel may be deposited so that an area called a white spot may occur, which is rendered as an area having higher brightness than the surrounding retinal layer area. Therefore, it is possible to detect the high brightness area by the threshold value process and to set the area as the candidate lesion.

Further, the candidate lesion detection unit 207 sends the candidate lesion information to the imaging position setting unit 208.

<Step S306>

In Step S306, the imaging position setting unit 208 sets the imaging position for imaging by the single line based on the coordinates of the central fossa MC stored in the memory unit 204 and the acquired candidate lesion information. An example of a specific setting method is described below.

In this embodiment, there is described a first method of setting the imaging position so as to acquire the tomographic image including a position at which a degree of abnormality of the candidate lesion becomes maximum.

Figure 5:
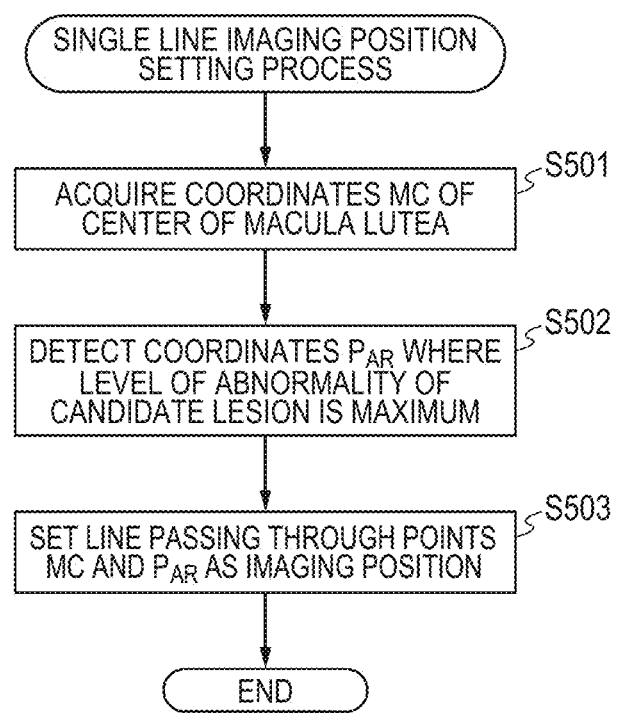
FIG. 5 is a flowchart illustrating a process procedure of a first setting method for a single line imaging position.

FIG. 5 is a flowchart illustrating a process procedure of the first method, and a specific setting method is described with reference to this flowchart.

<Step S501>

In Step S501, the imaging position setting unit 208 acquires coordinates of the center of the macula lutea MC from the memory unit 204.

<Step S502>

In Step S502, the imaging position setting unit 208 detects, in the acquired candidate lesion information, a position at which the degree of abnormality of the candidate lesion becomes maximum. Specifically, the imaging position setting unit 208 calculates an average value $n_{i,j}$ of normal layer thicknesses of the coordinates (i, j) based on the normal value database stored in the memory unit, and determines the coordinates (i, j) at which a difference between the average value $n_{i,j}$ and the layer thickness value $t_{i,j}$ becomes maximum. The determined coordinates are set to a point $P_{AR}$.

<Step S503>

In Step S503, the imaging position setting unit 208 sets a line passing through the two points MC and $P_{AR}$ as the imaging position.

Figure 6A:
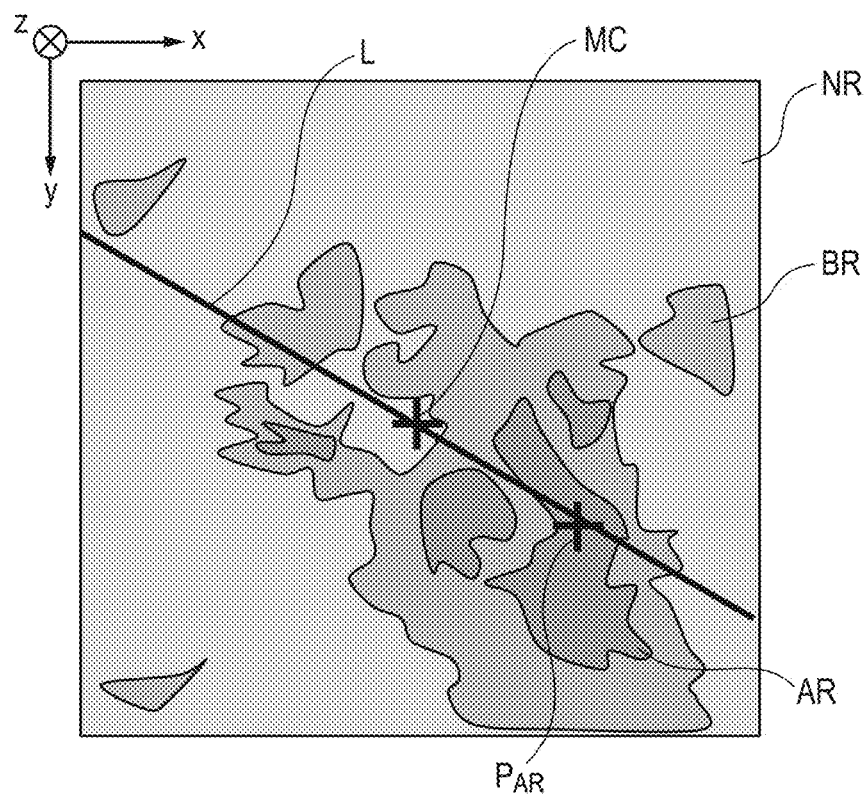
FIGS. 6A and 6B are diagrams illustrating a single line imaging position including a position of the maximum degree of abnormality of a candidate lesion and an acquired image.
Figure 6B:
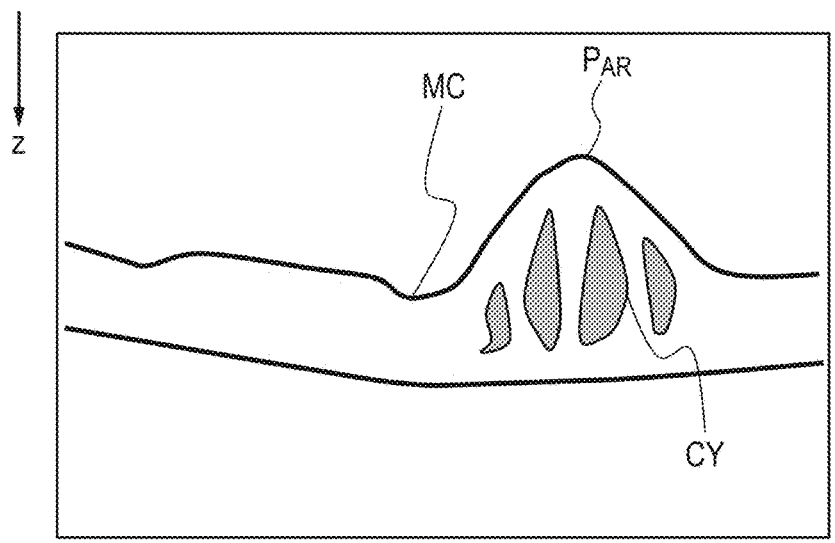

FIGS. 6A and 6B are diagrams illustrating the imaging position passing through the position at which the degree of abnormality of the candidate lesion becomes maximum, and the tomographic image to be acquired, respectively. FIG. 6A illustrates the significance map of the thickness of the retina, in which "AR", "BR", "NR", and "MC" represent the same items as in FIG. 4. The point $P_{AR}$ is the position at which the degree of abnormality of the candidate lesion becomes maximum, and the line L is a line passing through the two points MC and $P_{AR}$. FIG. 6B illustrates the tomographic image of the fundus taken at the position of the line L, in which "MC" and "$P_{AR}$" represent the same items as in FIG. 6A, and "CY" represents the cyst. It is understood that FIG. 6B illustrates a single tomographic image showing the center of the macula lutea and in particular, the region where the retina swells.

Thus, it is possible to set the imaging position so as to acquire the tomographic image including both the center of the macula lutea that is important for diagnosis of a macula lutea disease and the position where the degree of abnormality of the candidate lesion becomes maximum. This method is effective in a case where a large candidate lesion appears locally. This method is also effective in another case than the case where there is a part swelling locally due to macula lutea edema as illustrated in FIG. 6B, for example, in a case of polypoidal choroidal vasculopathy in which a polyp or an abnormal blood vessel network cause significant deformation of the retinal pigment epithelium.

Next, there is described a second method of setting the imaging position so as to acquire the tomographic image including the maximum area of the candidate lesion.

Figure 7:
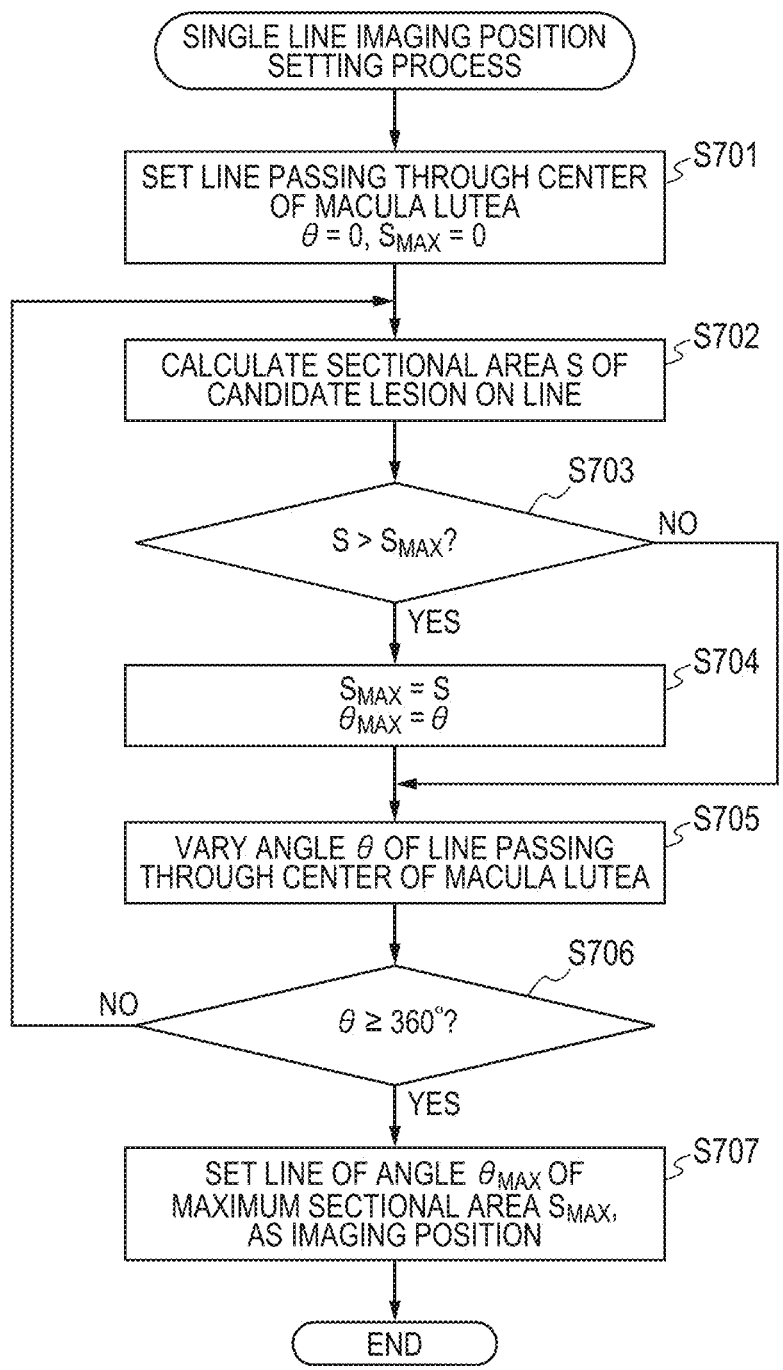
FIG. 7 is a flowchart illustrating a process procedure of a second setting method for the single line imaging position.

FIG. 7 is a flowchart illustrating a process procedure of the second method, and a specific setting method is described with reference to the flowchart.

<Step S701>

In Step S701, the imaging position setting unit 208 acquires the coordinates of the center of the macula lutea MC from the memory unit 204, and sets a line that passes through the center of the macula lutea MC and has an angle $\theta=0$ as an initial position of the imaging position L of the line scan. Further, the imaging position setting unit 208 sets a maximum value $S_{MAX}$ of a sectional area S described below to zero.

<Step S702>

In Step S702, the imaging position setting unit 208 associates, on the x-y plane, the acquired candidate lesion information with the position of the line L set in Step S701. Then, the imaging position setting unit 208 regards the candidate lesion information as volume data having a layer thickness value in the z direction with respect to the x-y plane, and calculates the sectional area S of the volume data of the candidate lesion crossed by the line L. In this case, when the line L does not pass through the candidate lesion, S=0 holds.

<Step S703>

In Step S703, the imaging position setting unit 208 compares the calculated sectional area S with the maximum value $S_{MAX}$ of the sectional area. When $S>S_{MAX}$ holds, the process proceeds to Step S704. When $S \leq S_{MAX}$ holds, the process proceeds to Step S705.

<Step S704>

In Step S704, the imaging position setting unit 208 updates the maximum value $S_{MAX}$ of the sectional area to the value S, and updates an angle $\theta_{MAX}$ of the line L corresponding to the maximum value to the current angle $\theta$ of the line L.

<Step S705>

In Step S705, the imaging position setting unit 208 varies the current angle $\theta$ of the line L. In this embodiment, 5 degrees are added to the value of $\theta$, for example.

<Step S706>

In Step S706, the imaging position setting unit 208 refers to a value of the current angle $\theta$ of the line L. When $\theta \geq 360°$ holds, the process proceeds to Step S707. When $\theta<360°$ holds, the process proceeds to Step S702.

<Step S707>

In Step S707, the imaging position setting unit 208 sets, as the imaging position of the line scan, the line L of the angle $\theta_{MAX}$ where the sectional area of the cross section passing through the candidate lesion takes the maximum value $S_{MAX}$.

In this way, the imaging position setting unit 208 includes a module functioning as a calculating unit for determining the candidate lesion area included in a cross section perpendicular to the fundus based on a result of the candidate lesion detection. Then, based on information obtained from the result, the imaging position setting unit 208 sets the imaging position of the line scan so that the candidate lesion area included in the cross section becomes maximum.

Figure 8A:
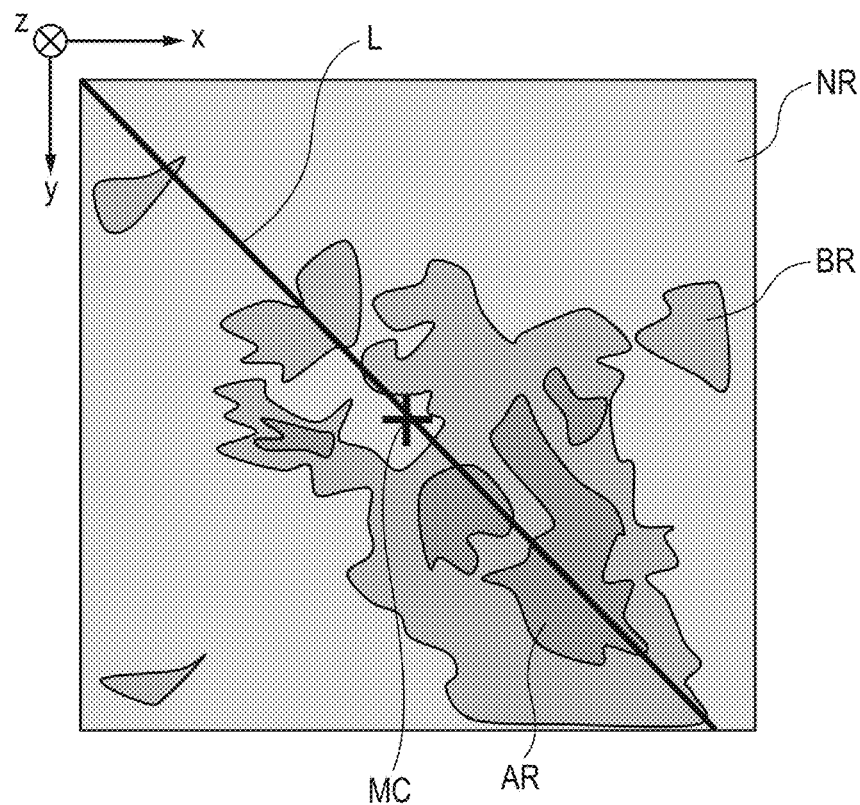
FIGS. 8A and 8B are diagrams illustrating a single line imaging position including the maximum area of the candidate lesion and an acquired image.
Figure 8B:
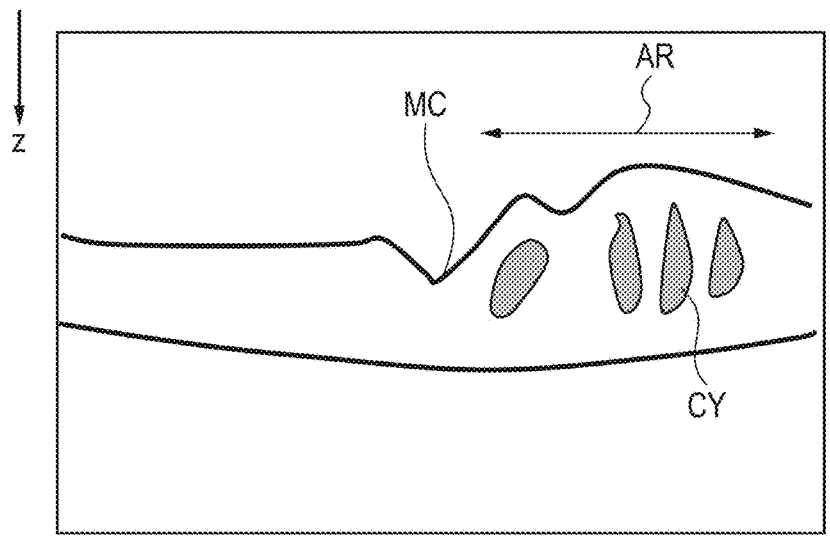

FIGS. 8A and 8B are diagrams illustrating the imaging position at which the sectional area of the cross section passing through the candidate lesion becomes maximum, and the acquired tomographic image. FIG. 8A illustrates a significance map of the thickness of the retina, in which "AR", "BR", "NR", and "MC" represent the same items as in FIG. 6A, and the line L is a line that passes through MC and has a maximum sectional area of the cross section passing through the candidate lesion. FIG. 8B illustrates a tomographic image of the fundus taken at the position of the line L, in which "AR" represents the candidate lesion area similarly to FIG. 8A, and "MC" and "CY" represent the same items as in FIG. 6B. It is understood that FIG. 8B illustrates a single tomographic image showing the center of the macula lutea and in particular, a region where a swelling area of the retina extends largely.

Thus, it is possible to set the imaging position so as to acquire the tomographic image including the center of the macula lutea that is important for diagnosis of a macula lutea disease and the maximum area of the candidate lesion. This method is effective in a case where a candidate lesion having a large size exists. This method is also effective in another case than the case where there is a part in which the swelling area of the retina due to the macula lutea edema extends largely as illustrated in FIG. 8B, for example, in a case of serious detachment of the retina in which the retina is lifted in a wide range.

Next, there is described a third method of setting the imaging position so as to acquire the tomographic image including the maximum number of candidate lesions.

Figure 9:
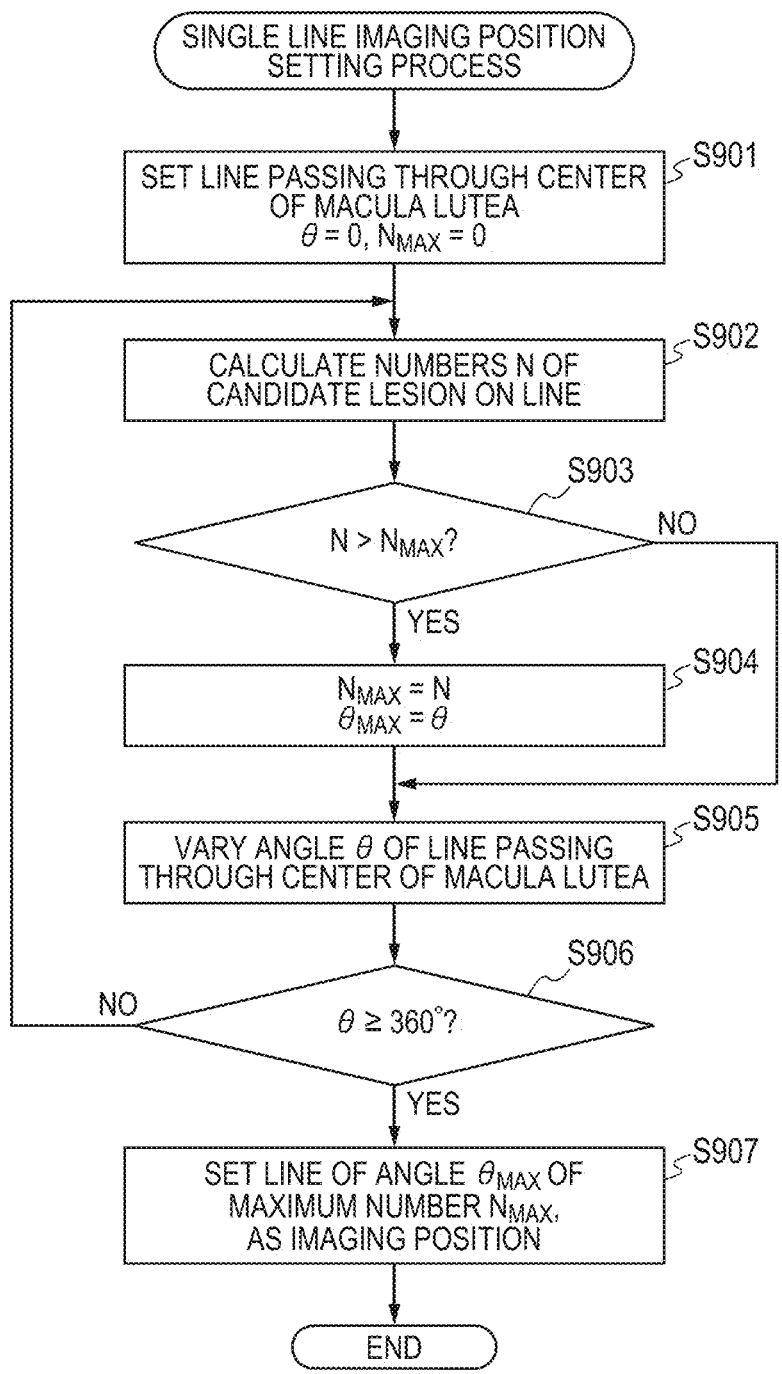
FIG. 9 is a flowchart illustrating a process procedure of a third setting method for the single line imaging position.

FIG. 9 is a flowchart illustrating a process procedure of the third method, and a specific method is described with reference to this flowchart. Here, it is supposed that "N" represents the number of candidate lesions through which the line L passes, and "$N_{MAX}$" represents the maximum value of "N". Then, this method corresponds to a method obtained by replacing the sectional area S in the second method with the number N and replacing the maximum value $S_{MAX}$ of the sectional area in the second method with the maximum value $N_{MAX}$ of the number N. Therefore, the specific description is omitted. However, the angle $\theta_{MAX}$ when the number of candidate lesions becomes "$N_{MAX}$" may not be determined uniquely. Therefore, as described below, in Step S904 of this embodiment, there is performed a process of selecting the line passing through the candidate lesions whose total sum of the sectional areas becomes maximum among the lines that pass through the maximum number $N_{MAX}$ of candidate lesions. A specific process in Step S904 is described below.

<Step S904>

In Step S904, the imaging position setting unit 208 calculates the sectional area S of the candidate lesions included on the line (in this case, the total sum of the sectional areas of multiple candidate lesions). Then, the calculated sectional area S is compared with the maximum value $S_{MAX}$ of the sectional area (an initial value thereof is zero). When $S>S_{MAX}$ holds, values are updated as $S_{MAX}=S$, $N_{MAX}=N$, and $\theta_{MAX}=\theta$. When $S \leq S_{MAX}$ holds, the values are not updated. Through the operation described above, the imaging position setting unit 208 as the acquiring position setting unit sets the acquiring position of the tomographic image based on a distribution of the number of candidate lesions.

In this way, the imaging position setting unit 208 determines the number of candidate lesions through which the line L passes, while varying the angle of the line L set on the fundus in a searching manner. Therefore, the imaging position setting unit 208 includes a module functioning as a calculating unit for determining the distribution of the number of candidate lesions based on a result of the candidate lesion detection. Then, based on the information obtained from the result, the imaging position of the line scan is set so that the number of candidate lesions included in the cross section becomes maximum.

Figure 10A:
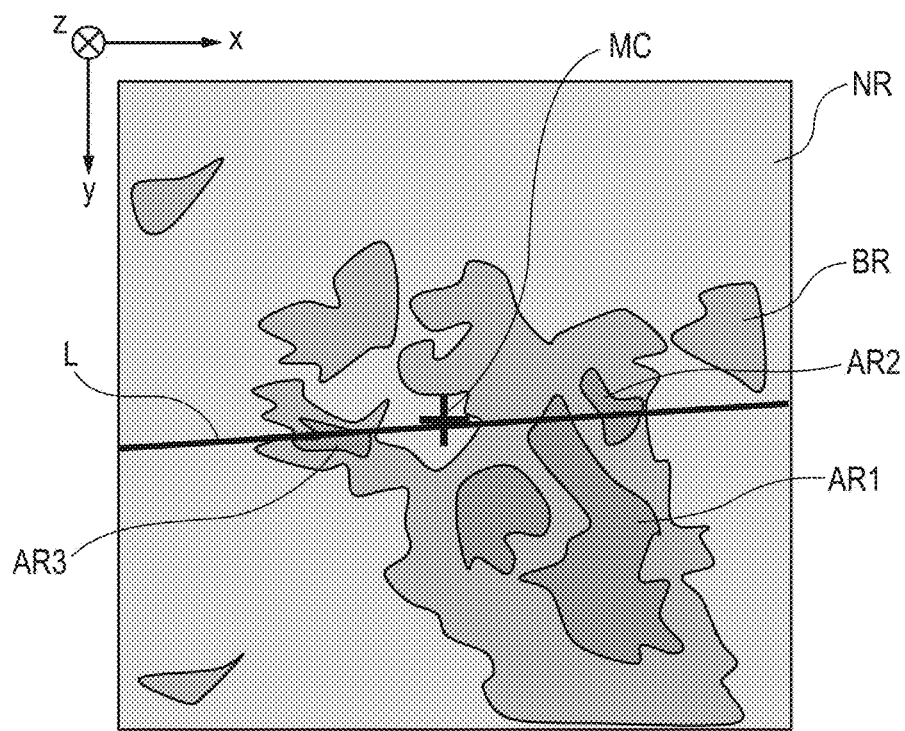
FIGS. 10A and 10B are diagrams illustrating a single line imaging position including the maximum number of the candidate lesions and an acquired image.
Figure 10B:
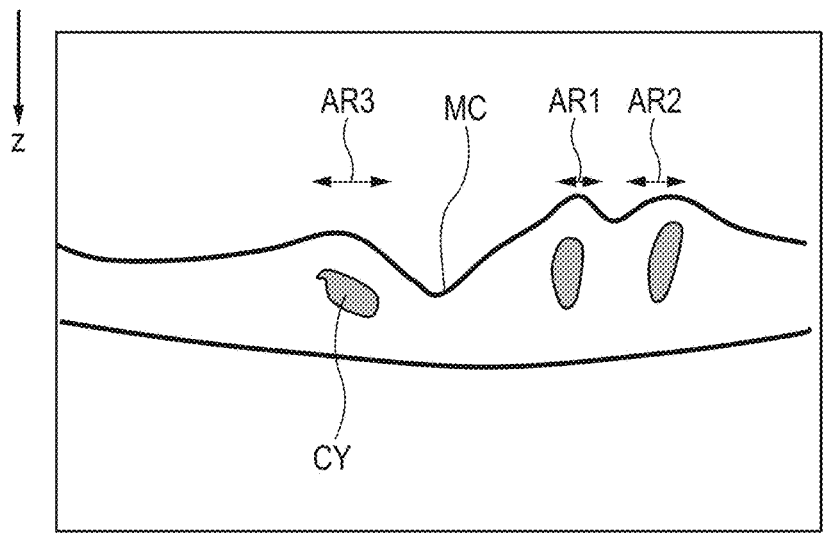

FIGS. 10A and 10B are diagrams illustrating the imaging position including a maximum number of the candidate lesions, and the acquired tomographic image. FIG. 10A illustrates a significance map of the thickness of the retina, in which "BR", "NR", and "MC" represent the same items as in FIG. 6A, and the line L is a line that passes through MC and has a maximum number of the candidate lesions. In addition, "AR1" to "AR3" represent different candidate lesion areas. FIG. 10B illustrates a tomographic image of the fundus taken at the position of the line L, in which "AR1" to "AR3" represent different candidate lesion areas similarly to FIG. 10A, and "MC" and "CY" represent the same items as in FIG. 6B. It is understood that FIG. 10B illustrates a single tomographic image showing the center of the macula lutea and three regions where the retina swells.

Thus, it is possible to set the imaging position so as to acquire the tomographic image including the center of the macula lutea and as many candidate lesions as possible. This method is effective in a case where a large number of relatively small candidate lesions exist. This method is also effective in another case than the case where the swelling areas of the retina due to the macula lutea edema are distributed as illustrated in FIG. 10B, for example, in a case of diabetic retinopathy in which many white spot areas are distributed in a wide range. In this case, in Step S305, the white spot areas are extracted as candidate lesions.

In addition, as described above, there are described three methods of setting the imaging position so as to include both the center of the macula lutea and the lesion region, but the present invention is not limited to the method for including the center of the macula lutea. It is possible to adopt a method in which the condition that the line passes through the center of the macula lutea is eliminated from the above-mentioned method. In this case, the imaging position specialized only in grasping the feature of the candidate lesion in the best manner is set.

Next, the imaging position setting unit 208 sends, to the tomographic imaging unit 203 and the display unit 209, the set position information of the line scan as a parameter for imaging.

<Step S307>

In Step S307, the display unit 209 acquires the fundus image B taken in real time and the alignment parameter from the fundus tracking unit 202, and further acquires the imaging position information of the single line acquired from the imaging position setting unit 208. Then, the display unit 209 indicates, on a monitor (not shown), the imaging position information of the single line while being superimposed on the fundus image B.

In this case, the imaging position information of the single line is determined based on the volume data of the 3D scan image taken in Step S303, and is associated with the coordinate system of the fundus image A. Therefore, the position information of the line scan is converted into the coordinate system of the fundus image B using the alignment parameter so that the coordinate system thereof matches with the coordinate system of the fundus image B.

According to the configuration described above, the candidate lesion is detected in the volume image, and, based on a result of the detection, the single line imaging position for the subsequent imaging is automatically determined so that the feature is best grasped. Thus, the tomographic image suitable for detailed observation of the candidate lesion can be easily taken without spending time and effort to manually search for the candidate lesion by the operator. In addition, it is possible to prevent overlooking of the candidate lesion by the operator. Further, when both the 3D scan and the line scan are used on a clinical site, the information of the volume image obtained by the 3D scan can be effectively used for determining the imaging position of the line scan.

Second Embodiment

In the first embodiment, there is described the method of automatically setting the single line imaging position. In this embodiment, there is described a case where the imaging position setting unit 208 of the first embodiment sets a multi-line imaging position constituted of multiple single lines. In the conventional method of setting the imaging position, the imaging position is set based on the candidate lesion range. Therefore, when an imaging position is set using spatially separate multiple lines, extension of the candidate lesion can be covered, but it is not necessarily possible to acquire the tomographic image useful for diagnosis of a lesion. Therefore, in this embodiment, the multi-line imaging position is automatically set so as to grasp features of the candidate lesion and to cover extension or distribution of the candidate lesions.

The configuration of the apparatus is the same as that of the first embodiment, and therefore description thereof is omitted. However, there is a difference in which the imaging position setting unit 208 of the first embodiment illustrated in FIG. 2 sets the single line imaging position while the imaging position setting unit 208 of the second embodiment sets the multi-line imaging position.

Figure 11:
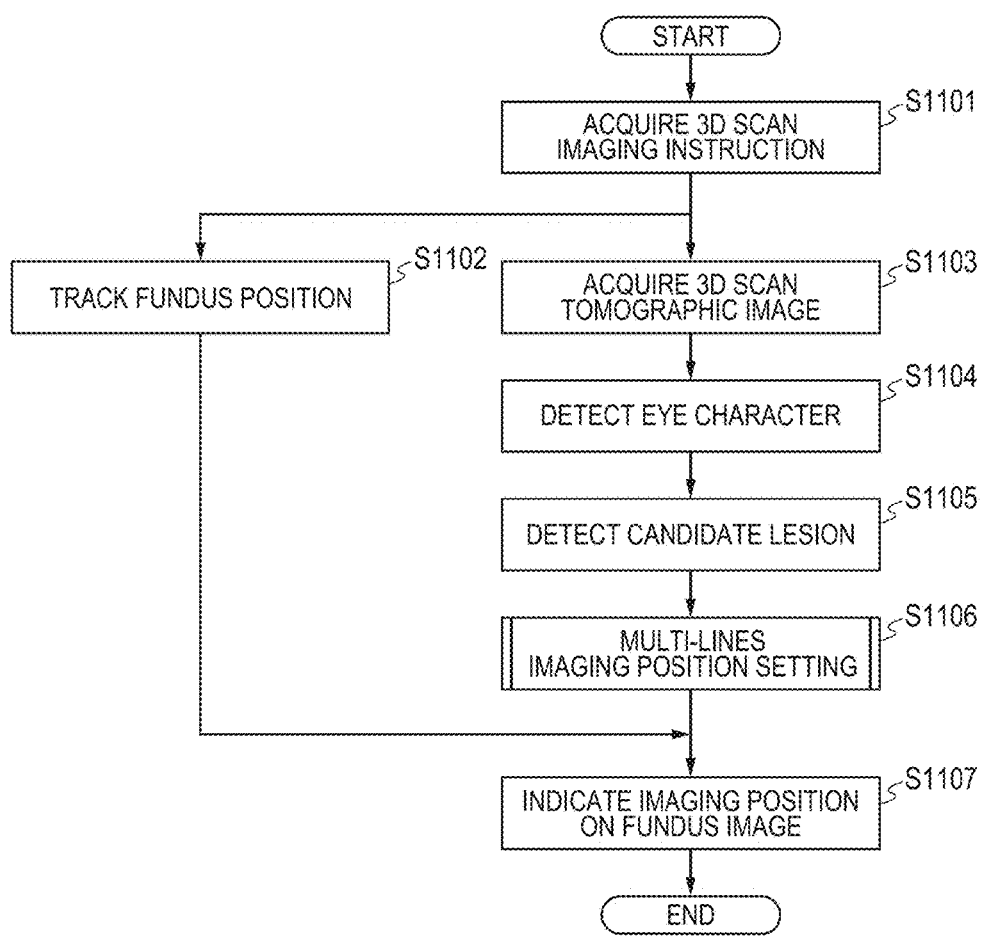
FIG. 11 is a flowchart illustrating a process procedure performed by an imaging support apparatus according to a second embodiment of the present invention.

FIG. 11 is a flowchart of this embodiment, and a specific process procedure performed by the imaging support apparatus 10 is described with reference to this flowchart. However, the process of Steps S1101 to S1105 and Step S1107 are the same as the process of Steps S301 to S305 and Step S307 in FIG. 3, and therefore description thereof is omitted.

<Step S1106>

In Step S1106, the imaging position setting unit 208 sets the imaging position for performing the multi-line scan based on the coordinates of the central fossa (center of macula lutea) MC stored in the memory unit 204 and the acquired candidate lesion information. In this embodiment, there is described below an example of a specific setting method, in which the number of the multiple lines is five.

In this embodiment, there is described a first method of setting the multi-line imaging position so as to acquire the tomographic image including a position at which a degree of abnormality of the candidate lesion becomes maximum. This method is applied to a case where the candidate lesion is significantly changed locally, similarly to the first method in Step S306 of the first embodiment.

Figure 12:
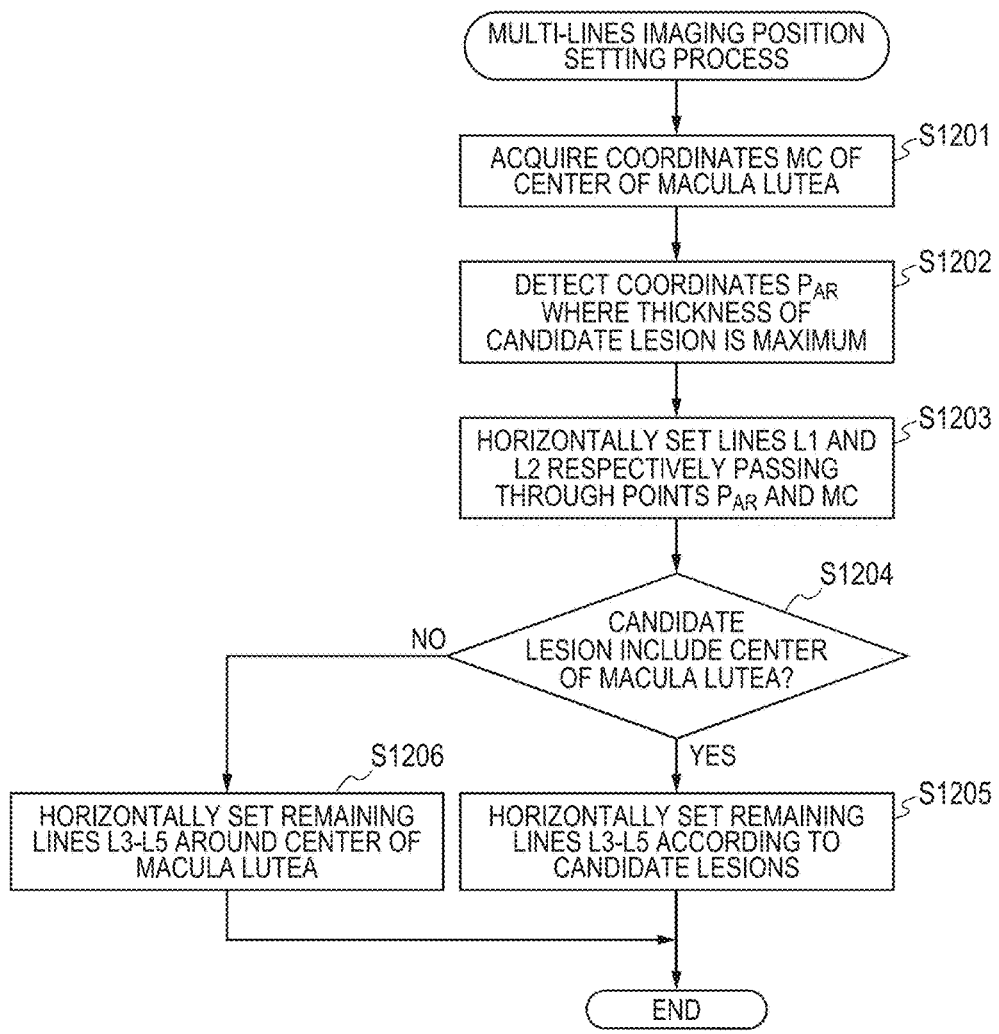
FIG. 12 is a flowchart illustrating a process procedure of a first setting method for a multi-line imaging position.

FIG. 12 is a flowchart illustrating a process procedure of the first method, and a specific setting method is described with reference to the flowchart. However, Steps S1201 and S1202 are the same as Steps S501 and S502 in FIG. 5, and therefore description thereof is omitted.

<Step S1203>

In Step S1203, the imaging position setting unit 208 sets two lines L1 and L2 passing through the point $P_{AR}$ and the point MC, respectively, in a horizontal direction.

<Step S1204>

In Step S1204, the imaging position setting unit 208 determines whether or not the candidate lesion area includes the center of the macula lutea. When the candidate lesion area includes the center of the macula lutea, the process proceeds to Step S1205. When the candidate lesion area does not include the center of the macula lutea, the process proceeds to Step S1206. In this way, the imaging position setting unit 208 includes a module functioning as a determination unit for determining whether or not the candidate lesion area of the fundus includes the center of macula lutea as the characteristic region.

<Step S1205>

In Step S1205, the imaging position setting unit 208 sets remaining lines L3 to L5 horizontally according to the candidate lesion area. Specifically, first, a y direction (vertical direction) range of the candidate lesion area in the x-y plane is set as "$R_Y$". Next, the lines L3 to L5 are uniformly set at equal intervals including the horizontal line L1 in the range $R_Y$. In this case, when the range $R_Y$ is very large, the line arrangement intervals become too separate. Therefore, a width of the range $R_Y$ is set as "$d_{AR}$", and an upper limit value $d_{MAX}$ is set for the value $d_{AR}$. Then, when the actual width $d_{AR}$ exceeds the upper limit value $d_{MAX}$, the width is corrected to be "$d_{MAX}$", and the lines L3 to L5 are set at equal intervals in a range having the width $d_{MAX}$ with reference to the line L1. In this embodiment, a width of 3.0 mm is adopted as the width $d_{MAX}$.

Figure 13A:
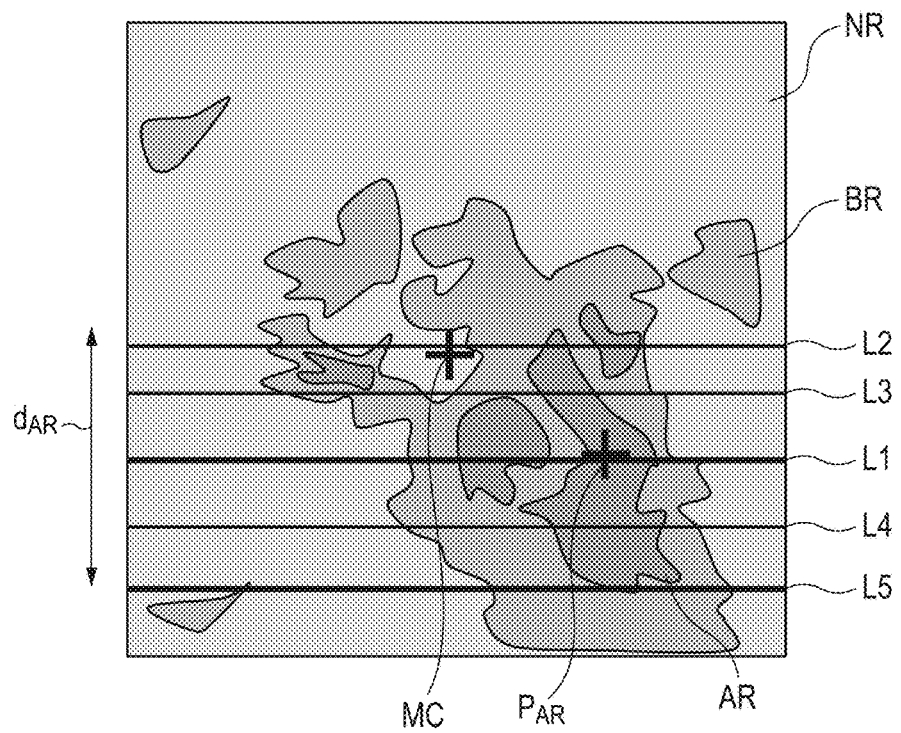
FIGS. 13A and 13B are diagrams illustrating a multi-line imaging position including a position of the maximum degree of abnormality of the candidate lesion.
Figure 13B:
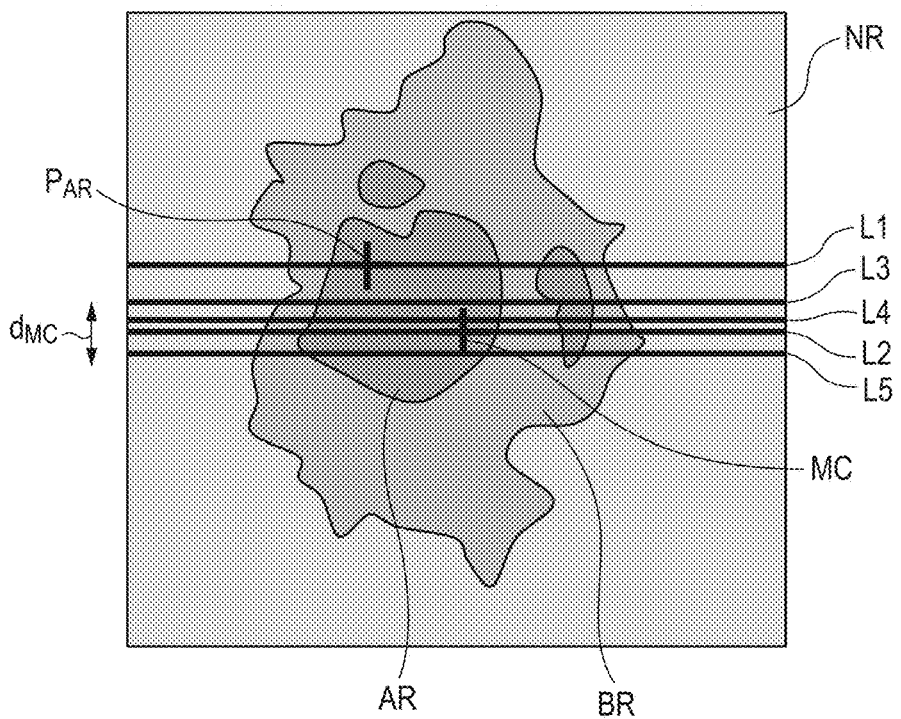

FIGS. 13A and 13B are diagrams illustrating the multi-line imaging position passing through the part at which the degree of abnormality of the candidate lesion becomes maximum. FIG. 13A is a diagram illustrating the multi-line imaging position superimposed on the significance map of the thickness of the retina in a case where the candidate lesion area does not includes the center of the macula lutea. In FIG. 13A, "AR" represents the candidate lesion area, "BR" represents the boundary area, "NR" represents the normal area, "MC" represents the center of the macula lutea, and "$P_{AR}$" represents the position at which the degree of abnormality of the candidate lesion is maximum. In addition, "L1" represents the horizontal line passing through the point $P_{AR}$, "L2" represents the horizontal line passing through the center of the macula lutea, "$d_{AR}$" represents a width of the candidate lesion area in the y direction, and "L3" to "L5" represent horizontal lines set in the range of "$d_{AR}$" with reference to the line L1. From this diagram, it is understood that the multiple lines are set so as to include the center of the macula lutea and the point at which the degree of abnormality of the candidate lesion becomes maximum, and to cover the entire candidate lesion area.

<Step S1206>

In Step S1206, the imaging position setting unit 208 sets the remaining lines L3 to L5 around the center of the macula lutea in the horizontal direction. Specifically, the lines are set at equal intervals in the range having a predetermined width $d_{MC}$ in the y direction (vertical direction) with reference to the horizontal line L2 passing through the point MC. In this embodiment, a width of 1.0 mm is adopted as the vertical width $d_{MC}$.

FIG. 13B is a diagram illustrating the multi-line imaging position superimposed on the significance map of the thickness of the retina in a case where the candidate lesion area includes the center of the macula lutea. In FIG. 13B, "AR", "BR", "NR", "MC", "$P_{AR}$", "L1", and "L2" represent the same items as in FIG. 13A. In addition, "$d_{MC}$" represents the predetermined width set around the center of the macula lutea, and "L3" to "L5" represent the horizontal lines set in the range of "$d_{MC}$" with reference to the line L2. From this diagram, it is understood that the multiple lines are set so as to include the center of the macula lutea and the point at which the degree of abnormality of the candidate lesion becomes maximum, and to cover the periphery of the center of the macula lutea.

Thus, it is possible to set the multi-line imaging position so as to acquire, at a usual imaging angle, the tomographic image including each of the center of the macula lutea and the position at which the degree of abnormality of the candidate lesion becomes maximum. Further, when the center of the macula lutea is not included in the candidate lesion area, the multi-line imaging position can be set so that the candidate lesion area can be observed uniformly. On the other hand, when the center of the macula lutea is included in the candidate lesion area, state observation of the center of the macula lutea is important. Therefore, the multi-line imaging position can be set so that the periphery of the center of the macula lutea can be observed in detail.

Next, there is described a second method of setting the multi-line imaging position so as to acquire the tomographic image including the maximum number of candidate lesion areas. This method is applied to a case where a candidate lesion having a large size exists similarly to the second method in Step S306 of the first embodiment.

FIG. 14 is a flowchart illustrating a process procedure of the second method, and a specific setting method is described with reference to the flowchart. However, Steps S1401 and S1404 are the same as Steps S1201 and S1204 in FIG. 12, and therefore description thereof is omitted.

<Step S1402>

In Step S1402, the imaging position setting unit 208 detects the line L1 where a sectional area of the cross section passing through the candidate lesion is maximum. In this embodiment, a line passing through a barycenter of the candidate lesion and having a maximum sectional area of the cross section passing through the candidate lesion is detected. This process corresponds to a process in which the center of the macula lutea in the second method of setting the single line imaging position, which is illustrated in FIG. 7, is replaced with the barycenter of the candidate lesion. Therefore, specific description thereof is omitted. However, it is not necessarily necessary that the line L1 pass through the barycenter of the candidate lesion, and the line L1 may be a line passing through the position at which the degree of abnormality of the candidate lesion becomes maximum.

<Step S1403>

In Step S1403, the imaging position setting unit 208 sets the line L2 passing through the point MC and in parallel with the line L1.

<Step S1405>

In Step S1405, the imaging position setting unit 208 sets the remaining lines L3 to L5 in parallel with the line L1 according to the candidate lesion area. This process corresponds to a process in which the process of setting the angle of lines set in Step S1205 is replaced with a process of setting the angle not horizontal but parallel with the line L1, and therefore specific description thereof is omitted.

Figure 15A:
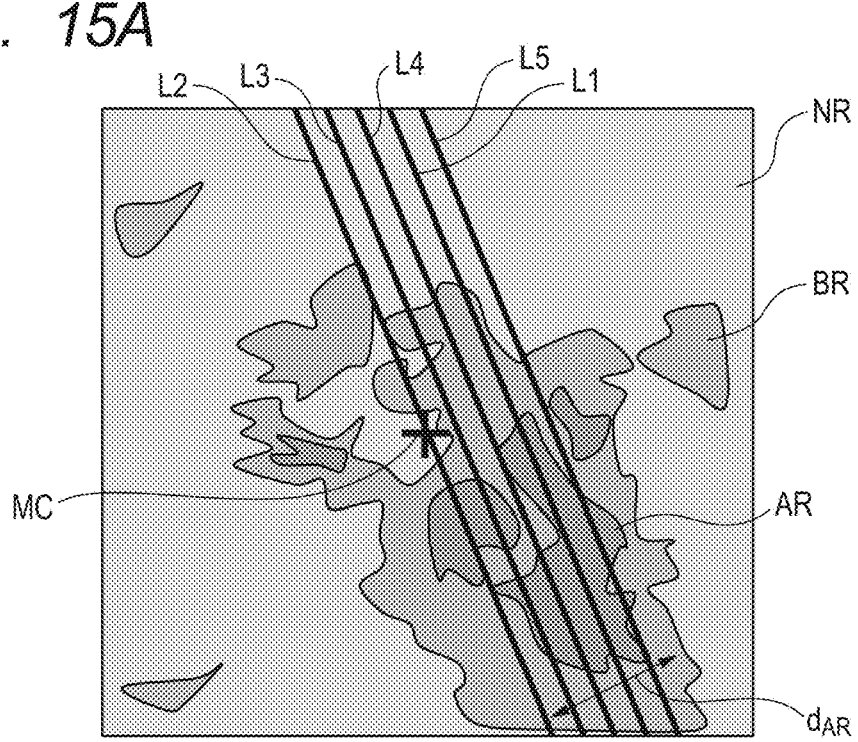
FIGS. 15A and 15B are diagrams illustrating a multi-line imaging position including the maximum area of the candidate lesion.
Figure 15B:
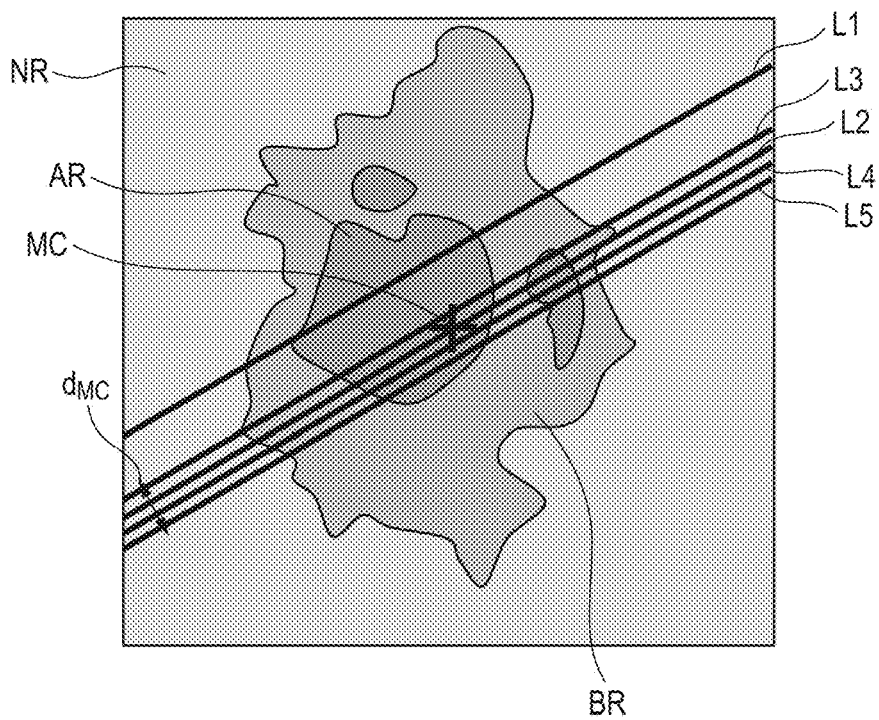

FIGS. 15A and 15B are diagrams illustrating the multi-line imaging position including the maximum number of candidate lesion areas. FIG. 15A is a diagram illustrating the multi-line imaging position superimposed on the significance map of the thickness of the retina in a case where the candidate lesion area does not include the center of the macula lutea. In FIG. 15A, "AR", "BR", "NR", and "MC" represent the same items as in FIG. 13A. In addition, "L1" represents a line passing through the candidate lesion area having a maximum sectional area, "L2" represents a line passing through the center of the macula lutea and set in parallel with the line L1, "$d_{AR}$" represents a width of the candidate lesion area in a direction perpendicular to the line L1, and "L3" to "L5" represent lines set in parallel with the line L1 in the range of "$d_{AR}$" with reference to the line L1. From this diagram, it is understood that the multiple lines are set so as to include the center of the macula lutea and the maximum number of candidate lesion areas, and to cover the entire candidate lesion area.

<Step S1406>

In Step S1406, the imaging position setting unit 208 sets the remaining lines L3 to L5 around the center of the macula lutea in parallel with the line L1. This process corresponds to a process in which the process of setting the angle of lines set in Step S1206 is replaced with the process of setting the angle not horizontal but parallel with the line L1, and therefore specific description thereof is omitted.

FIG. 15B is a diagram illustrating the multi-line imaging position superimposed on the significance map of the thickness of the retina in a case where the candidate lesion area includes the center of the macula lutea. In FIG. 15B, "AR", "BR", "NR", "MC", "L1", and "L2" represent the same items as in FIG. 15A. In addition, "$d_{MC}$" represents a predetermined width set around the center of the macula lutea in the direction perpendicular to the line L1, and "L3" to "L5" represent lines set in parallel with the line L2 in the range of "$d_{WC}$" with reference to the line L2. From this diagram, it is understood that the multiple lines are set so as to include the center of the macula lutea and the maximum number of candidate lesion areas, and to cover the periphery of the center of the macula lutea.

Thus, it is possible to set the multi-line imaging position so as to acquire each of the tomographic image including the center of the macula lutea and the tomographic image including the maximum number of candidate lesion areas. Further, when the center of the macula lutea is not included in the candidate lesion area, the multi-line imaging position can be set so that the entire candidate lesion that is more important for diagnosis can be observed. On the other hand, when the center of the macula lutea is included in the candidate lesion area, state observation of the center of the macula lutea is important. Therefore, the multi-line imaging position can be set so that the periphery of the center of the macula lutea can be observed in detail.

Next, there is described a third method of setting the multi-line imaging position so as to include the maximum number of candidate lesions. This method is applied to a case where a large number of relatively small candidate lesions exist similarly to the third method of Step S306 in the first embodiment.

Figure 16:
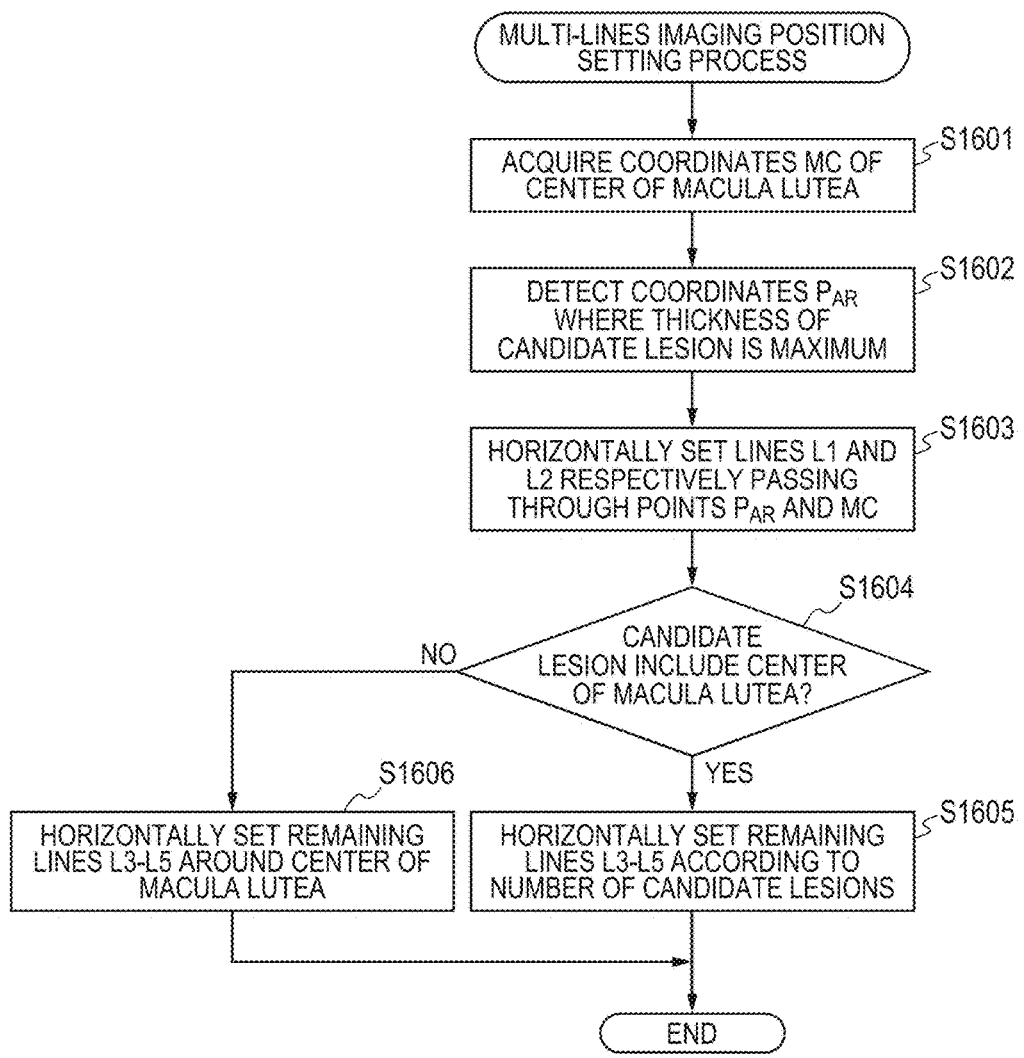
FIG. 16 is a flowchart illustrating a process procedure of a third setting method for the multi-line imaging position.

FIG. 16 is a flowchart illustrating a process procedure of the third method, and a specific setting method is described with reference to the flowchart. However, Steps S1601 to S1604 and S1606 are the same as Steps S1201 to S1204 and S1206 in FIG. 12, and therefore description thereof is omitted.

<Step S1605>

In Step S1605, the imaging position setting unit 208 sets the remaining lines L3 to L5 according to the number of candidate lesions. Specifically, the imaging position setting unit 208 detects, for each candidate lesion, a position where the degree of abnormality of the candidate lesion is maximum. However, the position where the degree of abnormality is maximum of all the candidate lesions is detected in Step S1602. Therefore, positions other than the above-mentioned position are detected for at most three candidate lesions. Then, the detected positions are set as points $P_{AR1}$, $P_{AR2}$, and $P_{AR3}$ in a descending order of the degree of abnormality of the candidate lesion, and the lines L3 to L5 are set so as to horizontally pass through the points $P_{AR1}$ to $P_{AR3}$, respectively.

Figure 17A:
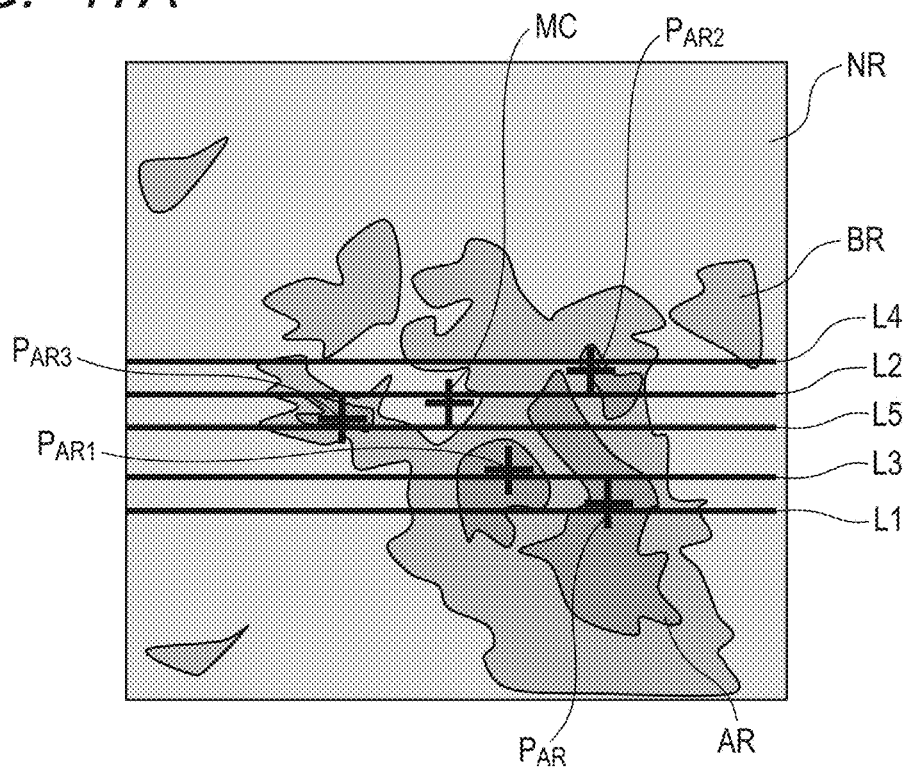
FIGS. 17A and 17B are diagrams illustrating a multi-line imaging position including the maximum number of the candidate lesions.
Figure 17B:
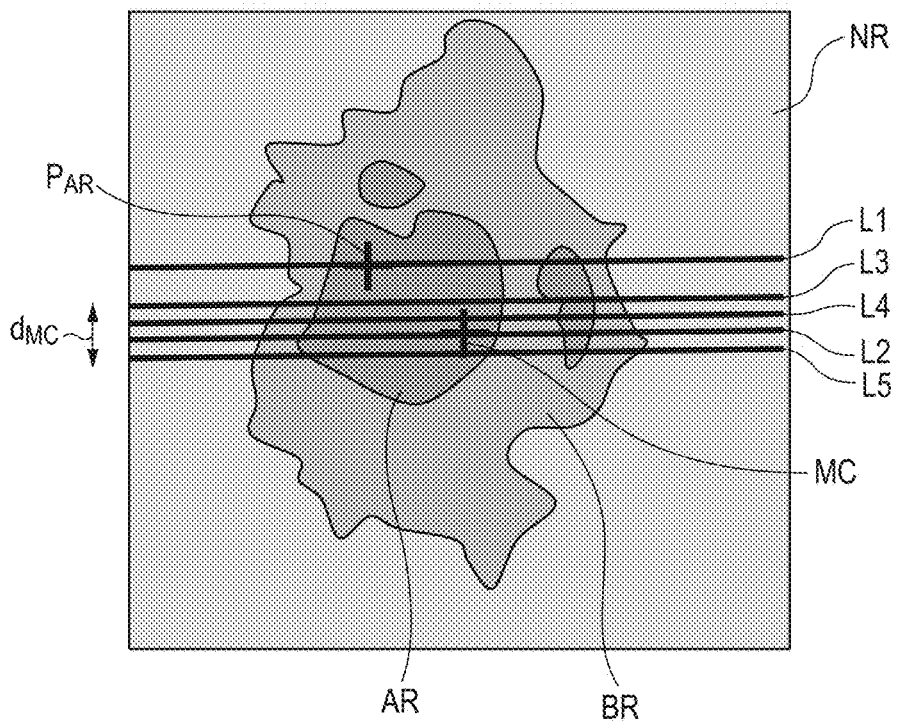

FIGS. 17A and 17B are diagrams illustrating the multi-line imaging position including the maximum number of candidate lesion areas. FIG. 17A is a diagram illustrating the multi-line imaging position superimposed on the significance map of the thickness of the retina in a case where the candidate lesion area does not include the center of the macula lutea. In FIG. 17A, "AR", "BR", "NR", and "MC" represent the same items as in FIG. 13A. In addition, "L1" and "L3" to "L5" represent horizontal lines passing through the positions at which the degree of abnormality of the respective candidate lesions becomes maximum, and "L2" represents a horizontal line passing through the center of the macula lutea. From this diagram, it is understood that the multiple lines are horizontally set so as to include the center of the macula lutea and as many candidate lesion areas as possible.

FIG. 17B is a diagram illustrating the multi-line imaging position superimposed on the significance map of the thickness of the retina in a case where the candidate lesion area includes the center of the macula lutea. This diagram is completely the same as FIG. 13B, and therefore description thereof is omitted.

Thus, it is possible to set the multi-line imaging position so as to acquire, at a usual imaging angle, the tomographic image including the center of the macula lutea and the maximum number of candidate lesions. Further, when the center of the macula lutea is not included in the candidate lesion area, the multi-line imaging position can be set so that as many lesions as possible can be observed. On the other hand, when the center of the macula lutea is included in the candidate lesion area, the multi-line imaging position can be set so that the periphery of the center of the macula lutea can be observed in detail.

In addition, there is described above the method of arranging all the multiple lines in parallel, but the present invention is not limited to this method. For instance, in FIG. 13A or 13B, it is possible to newly add vertical lines at positions corresponding to the positions at which the multiple lines are arranged horizontally. Thus, the imaging position can be set in the state where the multiple lines cross each other. Thus, the center of the macula lutea and the state of the candidate lesion can be grasped in more detail.

According to the configuration described above, the candidate lesion is detected in the volume image, and the multi-line imaging position for the subsequent imaging is automatically determined so that the feature is best grasped and the extension or distribution of the candidate lesion is covered. Thus, multiple tomographic images useful for diagnosis of the candidate lesion can be taken without spending time and effort to manually search for the candidate lesion by the operator. In addition, it is possible to prevent overlooking of the candidate lesion by the operator.

Third Embodiment

In the first and second embodiments, there are described the method of automatically setting the single line imaging position and the method of automatically setting the multi-line imaging position, respectively. In this embodiment, there is described a method of automatically setting the imaging position through automatic switching between the single line imaging method and the multi-line imaging method according to a situation. When the candidate lesion includes the center of the macula lutea, it is important that an influence of the candidate lesion to the center of the macula lutea can be observed in association with each other in the tomographic image in which the candidate lesion feature appears. On the other hand, when the candidate lesion area does not include the center of the macula lutea, there is basically no association between the candidate lesion and the center of the macula lutea. Therefore, it is not necessary that the influence of the candidate lesion to the center of the macula lutea can be observed in the same tomographic image. Further, when the imaging angle of the tomographic image on the fundus is not a usual imaging angle such as a horizontal or vertical angle, the operator may observe the tomographic image acquired at an imaging angle unfamiliar to the operator. Therefore, in this embodiment, when the candidate lesion includes the center of the macula lutea, the single line imaging position is set so that both the feature of the candidate lesion and the center of the macula lutea are rendered. When the candidate lesion does not include the center of the macula lutea, the multi-line imaging position is horizontally set so that the feature of the candidate lesion and the center of the macula lutea are rendered separately.

The configuration of the apparatus is the same as that of the first embodiment, and therefore description thereof is omitted. However, there is a difference in which the imaging position setting unit 208 of the first embodiment illustrated in FIG. 2 sets only the single line imaging position while the imaging position setting unit 208 of the third embodiment sets the imaging position through switching between the single line imaging method and the multi-line imaging method.

Figure 18:
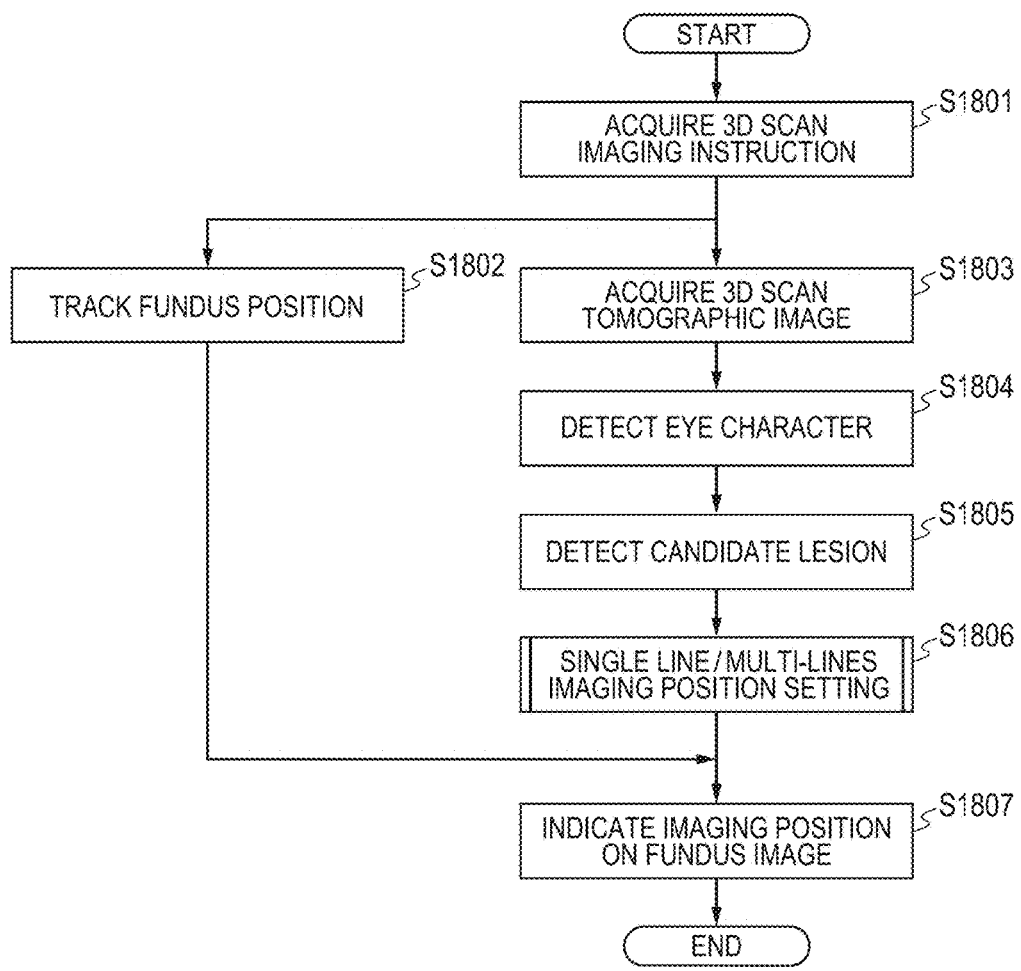
FIG. 18 is a flowchart illustrating a process procedure performed by an imaging support apparatus according to a third embodiment of the present invention.

FIG. 18 is a flowchart of this embodiment, and a specific process procedure performed by the imaging support apparatus 10 is described with reference to this flowchart. However, the process of Steps S1801 to S1805 and Step S1807 are the same as the process of Steps S301 to S305 and Step S307 in FIG. 3, and therefore description thereof is omitted.
<Step S1806>

In Step S1806, the imaging position setting unit 208 determines whether to perform imaging by the single line imaging method and the multi-line imaging method based on the coordinates of the central fossa (center of macula lutea) MC stored in the memory unit 204 and the acquired candidate lesion information. Then, when the single line imaging method is selected, the imaging position for performing the single line scan is set. When the multi-line imaging method is selected, the imaging position for performing the multi-line scan is set. In this embodiment, there is described below an example of a specific setting method, in which the number of the multiple lines is two.

Figure 19:
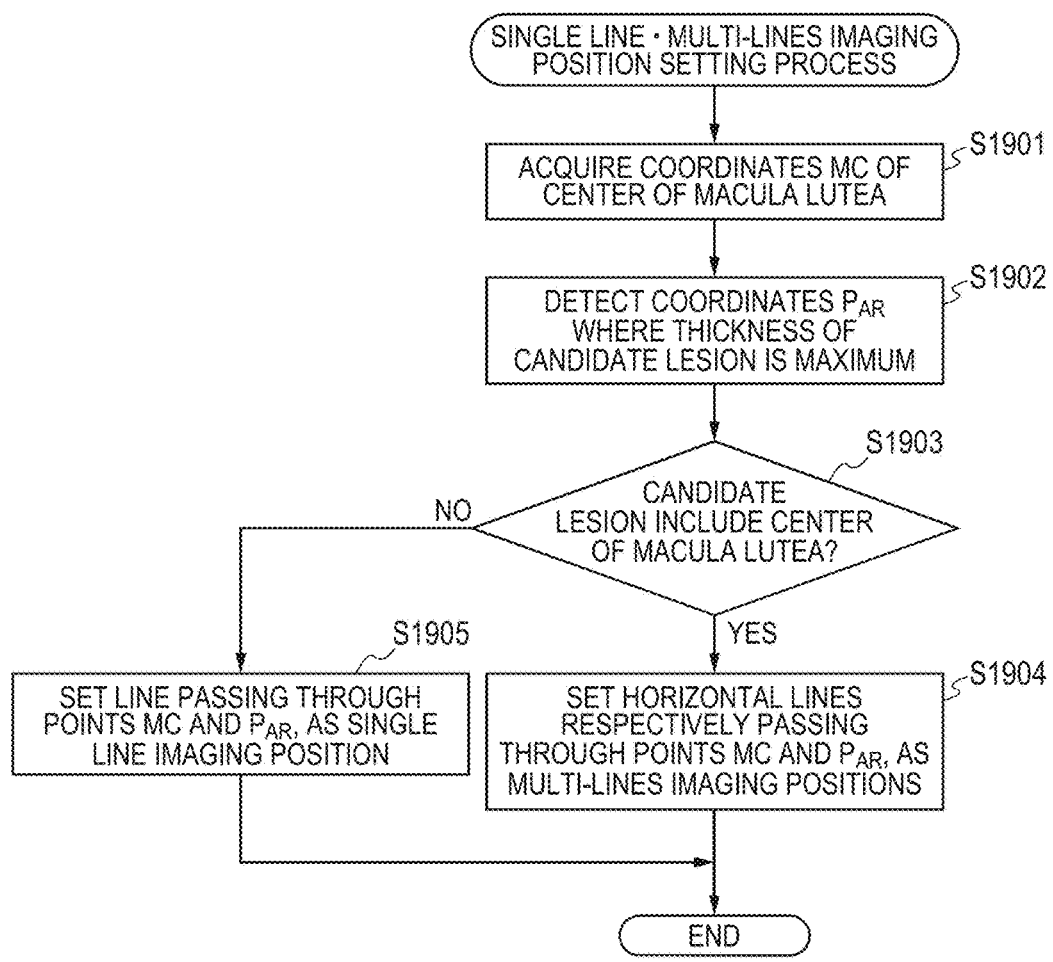
FIG. 19 is a flowchart illustrating a process procedure of a switch setting method for a single line/multi-line imaging position.

FIG. 19 is a flowchart illustrating a method of setting the imaging position through switching between the single line imaging method and the multi-line imaging method, and the specific setting method is described with reference to this flowchart. However, Steps S1901 and S1902 are the same as Steps S501 and S502 in FIG. 5, and therefore description thereof is omitted.
<Step S1903>

In Step S1903, the imaging position setting unit 208 determines whether or not the candidate lesion area includes the center of the macula lutea. When the candidate lesion area includes the center of the macula lutea, the process proceeds to Step S1904. When the candidate lesion area does not include the center of the macula lutea, the process proceeds to Step S1905.
<Step S1904>

In Step S1904, the imaging position setting unit 208 sets two lines L1 and L2 passing through the point $P_{AR}$ and the point MC, respectively, in the horizontal direction.

Figure 20A:
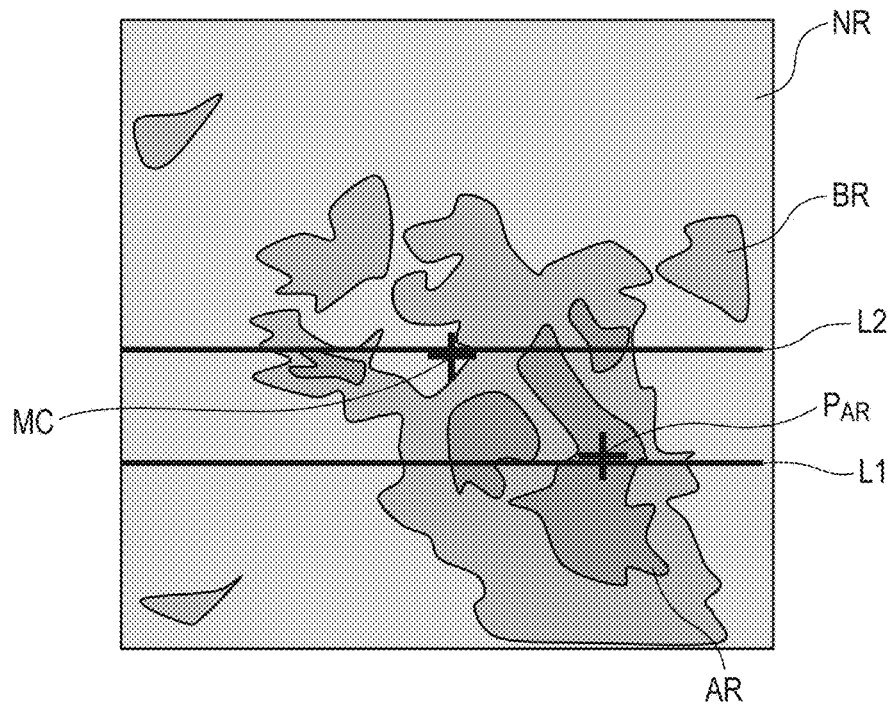
FIGS. 20A and 20B are diagrams illustrating the multi-line imaging position and the single line imaging position based on a positional relationship between the candidate lesion and the center of a macula lutea.
Figure 20B:
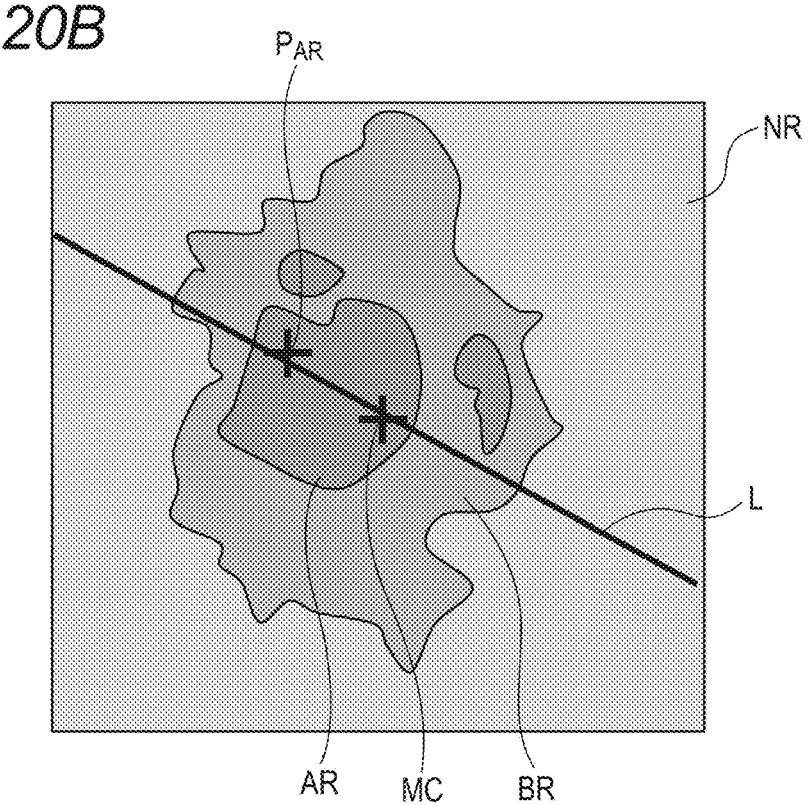

FIGS. 20A and 20B are diagrams illustrating the imaging positions set through switching between the single line imaging method and the multi-line imaging method. FIG. 20A is a diagram illustrating the imaging position set when the multi-line imaging method is selected as the imaging method. In FIG. 20A, "AR" represents the candidate lesion area, "BR" represents the boundary area, "NR" represents the normal area, "MC" represents the center of the macula lutea, and "$P_{AR}$" represents the position at which the degree of abnormality of the candidate lesion is maximum. In addition, "L1" represents the horizontal line passing through the point $P_{AR}$, and "L2" represents the horizontal line passing through the center of the macula lutea. From this diagram, it is understood that the candidate lesion and the center of the macula lutea are imaged through line scan using two different lines in a case where the candidate lesion area does not include the center of the macula lutea.

Thus, the tomographic image including the candidate lesion and the tomographic image including the center of the macula lutea can be observed as images taken at a usual imaging angle that is familiar to the operator.

<Step S1905>

In Step S1905, the imaging position setting unit 208 sets the line L passing through both the point $P_{AR}$ and the point MC.

FIG. 20B is a diagram illustrating the imaging position set when the single line imaging method is selected as the imaging method. In FIG. 20B, "AR", "BR", "NR", "MC", and "$P_{AR}$" represent the same items as in FIG. 20A. In addition, "L" represents the line passing through both the point $P_{AR}$ and the point MC. From this diagram, it is understood that the tomographic image is taken by the single line imaging method so that the candidate lesion and the center of the macula lutea are included in the same line in a case where the candidate lesion area includes the center of the macula lutea.

Thus, in a single tomographic image, the candidate lesion and the state of the center of the macula lutea can be observed in association with each other.

According to the configuration described above, the candidate lesion is detected in the volume image. Then, the imaging method is selected from the single line imaging method and the multi-line imaging method based on a positional relationship between the candidate lesion area and the center of the macula lutea so that the imaging position is automatically set by the selected imaging method. Thus, the operator can observe the tomographic image on the candidate lesion and the center of the macula lutea according to the situation with the number of images suitable for detailed observation of the candidate lesion.

Fourth Embodiment

In the first to third embodiments, there are described the methods of taking the volume image and automatically setting the imaging position of the line scan based on the candidate lesion detected in the tomographic image. In this embodiment, there is described a method of extracting not the imaging position of the line scan but the tomographic image from the volume image and automatically setting the position on the fundus for displaying the image on the monitor, to thereby display the image. Conventionally, when determining the tomographic image to be observed on the monitor after taking the volume image, the operator needs to spend time and effort to search for an appropriate slice from the volume image. Therefore, in this embodiment, the volume image is taken, and the candidate lesion detected in the tomographic image is analyzed. Thus, the display position on the fundus can be automatically set so as to display the tomographic image in which the feature of the candidate lesion is best grasped.

Figure 21:
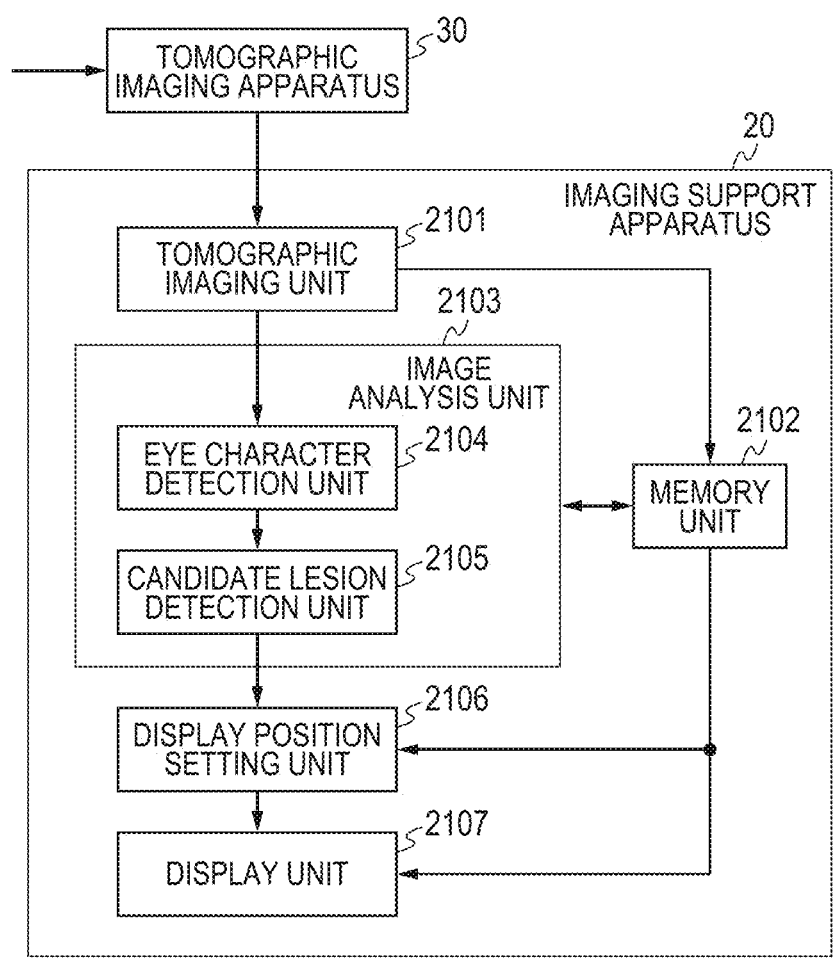
FIG. 21 is a diagram illustrating a functional configuration of a diagnosis support apparatus according to a fourth embodiment of the present invention.

FIG. 21 illustrates a functional configuration of a diagnosis support apparatus 20 according to this embodiment. In FIG. 21, a tomographic imaging apparatus 30 is provided together with the diagnosis support apparatus 20 including a tomographic image acquiring unit 2101, a memory unit 2102, an image analysis unit 2103, a display position setting unit 2106, and a display unit 2107. In addition, the image analysis unit 2103 includes an eye character detection unit 2104 and a candidate lesion detection unit 2105. Note that, the display position setting unit 2106 includes a module having a function of setting a display position of the tomographic image of the fundus included in the wide-range image of the fundus through the same operation as that of the acquiring position setting unit of the first to third embodiments.

Figure 22:
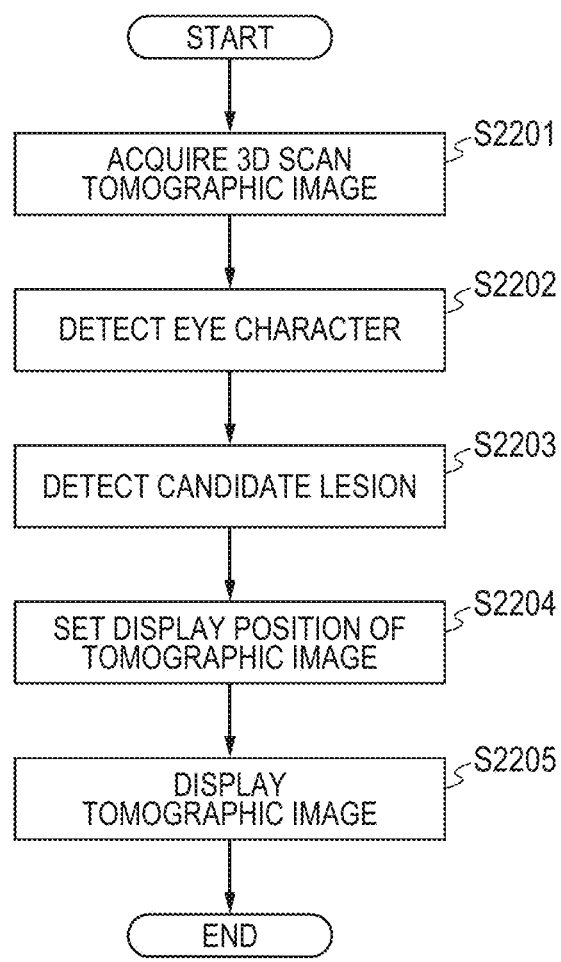
FIG. 22 is a flowchart illustrating a process procedure performed by the diagnosis support apparatus according to the fourth embodiment.

FIG. 22 is a flowchart of this embodiment, and a specific process procedure performed by the diagnosis support apparatus 20 is described with reference to this flowchart. However, the process of Steps S2202 and S2203 are the same as the process of Steps S304 and S305 in FIG. 3, and therefore description thereof is omitted.

<Step S2201>

In Step S2201, the tomographic image acquiring unit 2101 acquires the volume image from the tomographic imaging apparatus 30 based on an instruction of the operator (not shown), and sends the volume image to the memory unit 2102 and the eye character detection unit 2104.

<Step S2204>

In Step S2204, the display position setting unit 2106 automatically sets the display position of the tomographic image based on the candidate lesion information acquired from the candidate lesion detection unit 2105. In this case, the setting method of this embodiment corresponds to a process in which the single line imaging position set in Step S306 of the first embodiment is replaced with the display position of the tomographic image, and therefore specific description thereof is omitted.

However, the display position determined in this step is not limited to a single position. For instance, it is possible to adopt a method of setting three types of display positions by the same method as the method of setting three types of imaging positions, which is described in Step S306.

<Step S2205>

In Step S2205, the display unit 2107 displays the tomographic image corresponding to the display position information of the tomographic image, which is set by the display position setting unit 2106, in the volume image acquired from the memory unit 2102.

In this case, when the display position set by the display position setting unit 2106 is a single position, the tomographic image corresponding to the position is displayed as it is. On the other hand, when there are multiple display positions set by the display position setting unit 2106, the multiple display positions thus set are indicated so that the operator can select any one of the display positions. However, it is possible to set in advance any one of the multiple display positions as an initially indicated position so as to indicate first the initially indicated position thus set and then select another display position.

According to the configuration described above, the candidate lesion is detected in the volume image. Then, the display position of the tomographic image to be displayed is automatically determined so that the feature is best grasped, and the tomographic image is displayed. Thus, it is possible to save time and effort to search for the tomographic image suitable for detailed observation of the candidate lesion from the volume image, and it is also possible to prevent overlooking of the candidate lesion.

Other Embodiments

In the first to fourth embodiments, the candidate lesion is detected in the volume image so as to determine the position of the tomographic image to be taken or displayed, but the image in which the candidate lesion is detected is not limited to the volume image. For instance, it is possible to detect the candidate lesion in a 2D fundus image. Specifically, microaneurysm as an abnormal retinal blood vessel is rendered on the 2D fundus image, and hence is detected as the candidate lesion. First, the blood vessel area is extracted from the 2D fundus image by the method described in Step S302 of the first embodiment, and then the blood vessel diameter is compared with the normal value so that an area having a predetermined diameter or larger is detected as the microaneurysm. Then, the position of the tomographic image to be taken or displayed is determined so that the tomographic image in which the feature of the microaneurysm appears best can be observed. Thus, when determining the position of the line scan, time and effort for taking the 3D scan image in advance can be saved. In addition, when determining the position on the fundus for displaying the tomographic image on the monitor, the fundus image is analyzed so that calculation cost can be reduced further than in the case where the volume image is analyzed, and hence the time required for displaying the tomographic image can be reduced.

Further, it is needless to say that the object of the present invention can also be achieved with the following configuration. A software program code for implementing the functions of the above-mentioned embodiments is stored on a storage medium, and the storage medium is supplied to a system or an apparatus. Then, a computer (CPU or MPU) of the system or the apparatus reads out and executes the program code stored on the storage medium.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-168603, filed Aug. 1, 2011, which is hereby incorporated by reference herein in its entirety.

The invention claimed is:

1. An apparatus comprising:
   an acquiring unit configured to acquire a volume image of a retina;
   a detection unit configured to detect a plurality of candidate lesions in the volume image by analyzing the volume image;
   a determining unit configured to determine a distribution of the plurality of candidate lesions based on a result of the detection of the plurality of candidate lesions; and
   a setting unit configured to set, based on the distribution of the plurality of candidate lesions, a single line used for displaying a tomographic image of the retina, the single line being a straight line that passes through a macula lutea and the plurality of candidate lesions.

2. The apparatus according to claim 1, wherein the setting unit sets, as a position of the tomographic image of the retina to be displayed, the single line.

3. The apparatus according to claim 1, wherein the single line is a straight line indicating a position of the tomographic image that has therein a maximum number of the candidate lesions.

4. The apparatus according to claim 1, wherein the setting unit sets a plurality of straight lines, each of the straight lines indicating one position of a respective one of tomographic images of the retina,
   wherein one of the plurality of lines is the single line, and
   wherein a tomographic image of another of the plurality of lines does not intersect with the tomographic image of the single line.

5. The apparatus according to claim 1, further comprising an analysis unit that detects candidate lesions in the volume image by analyzing the volume image.

6. An apparatus according to claim 1, wherein the macula lutea is detected by using an anatomical feature that a center of the macula lutea is a dent area on a fundus.

7. A method comprising:
   acquiring a volume image of a retina;
   detecting a plurality of candidate lesions in the volume image by analyzing the volume image;
   determining a distribution of the plurality of candidate lesions based on a result of the detecting of the plurality of candidate lesions; and
   setting, based on the distribution of the plurality of candidate lesions, a single line used for displaying a tomographic image of the retina, the single line being a straight line that passes through a macula lutea and the plurality of candidate lesions.

8. A program for causing a computer to function as the apparatus according to claim 1.

9. A computer-readable medium having the program according to claim 8 stored thereon.

10. An apparatus comprising:
    an acquiring unit configured to acquire a volume image of a retina;
    a detection unit configured to detect a plurality of candidate lesions in the volume image by analyzing the volume image;
    a determining unit configured to determine a distribution of the plurality of candidate lesions based on a result of the detection of the plurality of candidate lesions; and
    a setting unit configured to set, based on the distribution of the plurality of candidate lesions, a single line used for imaging a tomographic image of the retina, the single line being a straight line that passes through a macula lutea and the plurality of candidate lesions.

11. The apparatus according to claim 10, wherein the single line is a straight line indicating a position of the tomographic image that has a maximum number of the candidate lesions.

12. The apparatus according to claim 10, further comprising an analysis unit that detects candidate lesions in the volume image by analyzing the volume image.

* * * * *